(12) United States Patent
Levi

(10) Patent No.: US 11,850,148 B2
(45) Date of Patent: Dec. 26, 2023

(54) SEALING MEMBER FOR PROSTHETIC HEART VALVE

(71) Applicant: Edwards Lifesciences Corporation, Irvine, CA (US)

(72) Inventor: Tamir S. Levi, Zikhron Yaakov (IL)

(73) Assignee: EDWARDS LIFESCIENCES CORPORATION, Irvine, CA (US)

(*) Notice: Subject to any disclaimer, the term of this patent is extended or adjusted under 35 U.S.C. 154(b) by 826 days.

(21) Appl. No.: 16/935,722

(22) Filed: Jul. 22, 2020

(65) Prior Publication Data

US 2020/0345488 A1 Nov. 5, 2020

Related U.S. Application Data

(62) Division of application No. 16/103,985, filed on Aug. 16, 2018, now Pat. No. 10,722,353.

(Continued)

(51) Int. Cl.
*A61F 2/24* (2006.01)

(52) U.S. Cl.
CPC .......... *A61F 2/2418* (2013.01); *A61F 2/2409* (2013.01); *A61F 2/2433* (2013.01); *A61F 2/2436* (2013.01); *A61F 2210/0014* (2013.01); *A61F 2220/0008* (2013.01); *A61F 2220/0025* (2013.01); *A61F 2220/0075* (2013.01);
(Continued)

(58) Field of Classification Search
CPC ......... A61F 2/24; A61F 2/2418; A61F 2/2433
See application file for complete search history.

(56) References Cited

U.S. PATENT DOCUMENTS

| 3,409,013 A | 11/1968 | Berry |
| 3,548,417 A | 12/1970 | Kisher |

(Continued)

FOREIGN PATENT DOCUMENTS

| DE | 0144167 C | 9/1903 |
| DE | 2246526 A1 | 3/1973 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

(Continued)

*Primary Examiner* — Matthew W Schall
(74) *Attorney, Agent, or Firm* — Edwards Lifesciences; Linda Allyson Nassif

(57) ABSTRACT

An implantable prosthetic valve can comprise an annular frame comprising an inflow end and an outflow end and being radially collapsible and expandable between a radially collapsed configuration and a radially expanded configuration, the frame defining an axial direction extending from the inflow end to the outflow end, a leaflet structure positioned within the frame and secured thereto, and an outer sealing member positioned around an outer surface of the frame, wherein the outer sealing member comprises a plurality of sealing segments, wherein each sealing segment is coupled to the frame and/or another sealing segment by a tether that pulls a portion of the sealing segment in a circumferential direction when the frame is radially expanded to the expanded configuration.

20 Claims, 15 Drawing Sheets

Related U.S. Application Data

(60) Provisional application No. 62/548,280, filed on Aug. 21, 2017.

(52) U.S. Cl.
CPC . *A61F 2230/001* (2013.01); *A61F 2230/0019* (2013.01); *A61F 2230/0054* (2013.01); *A61F 2250/0039* (2013.01); *A61F 2250/0063* (2013.01); *A61F 2250/0069* (2013.01)

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |

(56) References Cited

U.S. PATENT DOCUMENTS

| | | |
|---|---|---|
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0049313 A1 | 2/2010 | Alon et al. |
| 2010/0082094 A1 | 4/2010 | Quadri et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0004299 A1 | 1/2011 | Essinger et al. |
| 2011/0015729 A1 | 1/2011 | Jimenez et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Tariton |
| 2013/0317598 A1 | 11/2013 | Rowe et al. |
| 2013/0331929 A1 | 12/2013 | Mitra et al. |
| 2014/0128968 A1 | 5/2014 | Benichou et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2014/0371842 A1 | 12/2014 | Marquez et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2016/0199180 A1 | 7/2016 | Zeng et al. |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |

(56) References Cited

FOREIGN PATENT DOCUMENTS

| | | |
|---|---|---|
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 0018333 A1 | 4/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 A1 | 4/2005 |
| WO | 2005055883 A1 | 6/2005 |
| WO | 2005084595 A1 | 9/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |

OTHER PUBLICATIONS

H.R. Andersen "History of Percutaneous Aortic Valve Prosthesis," Herz No. 34. pp. 343-346. 2009.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Bailey, S. "Percutaneous Expandable Prosthetic Valves," Textbook of Interventional Cardiology vol. 2, 2nd Ed. pp. 1268-1276. 1994.
Al-Khaja, et al. "Eleven Years' Experience with Carpentier-Edwards Biological Valves in Relation to Survival and Complications," European Journal of Cardiothoracic Surgery, vol. 3. pp. 305-311. 1989.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Wheatley, "Valve Prostheses," Operative Surgery, 4th ed. pp. 415 424. 1986.
Uchida, "Modifications of Gianturco Expandable Wire Stents," American Journal of Roentgenology, vol. 150. pp. 1185-1187. 1986.

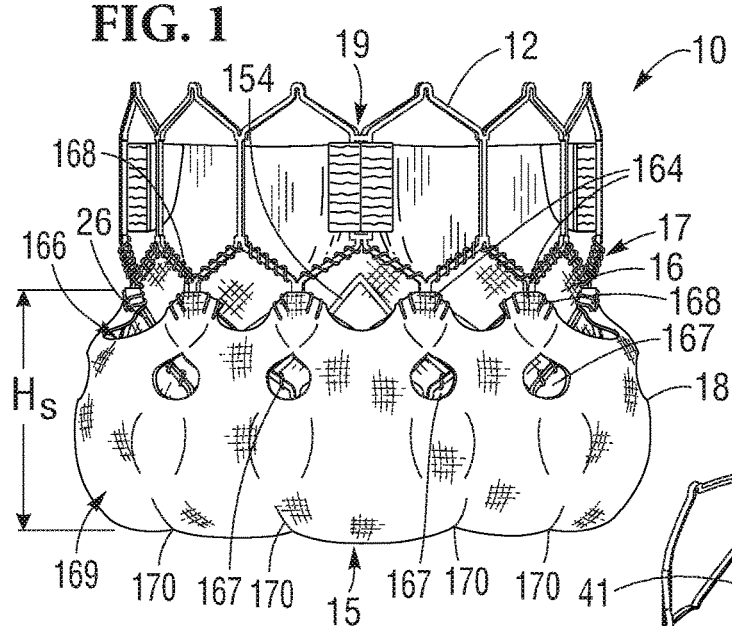
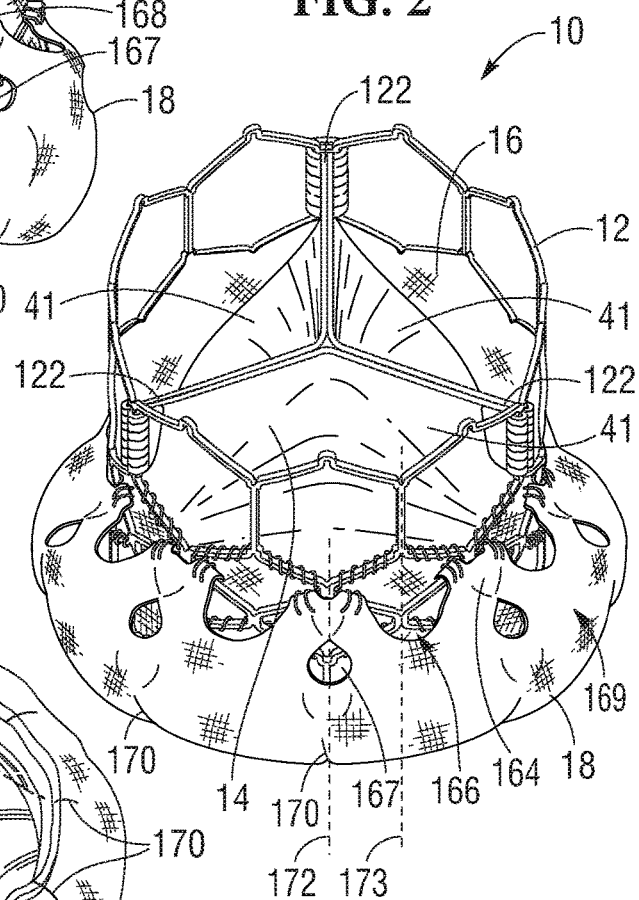
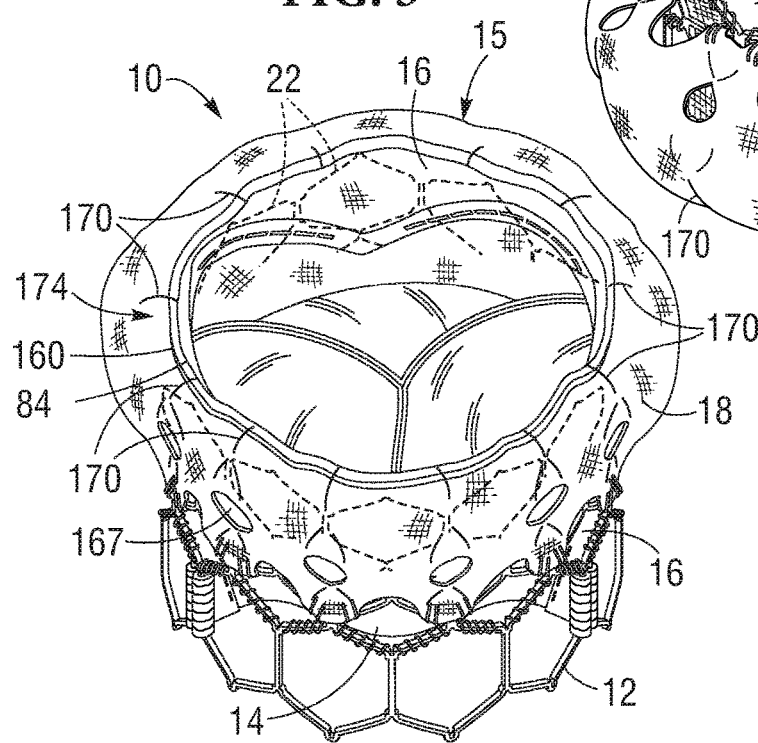

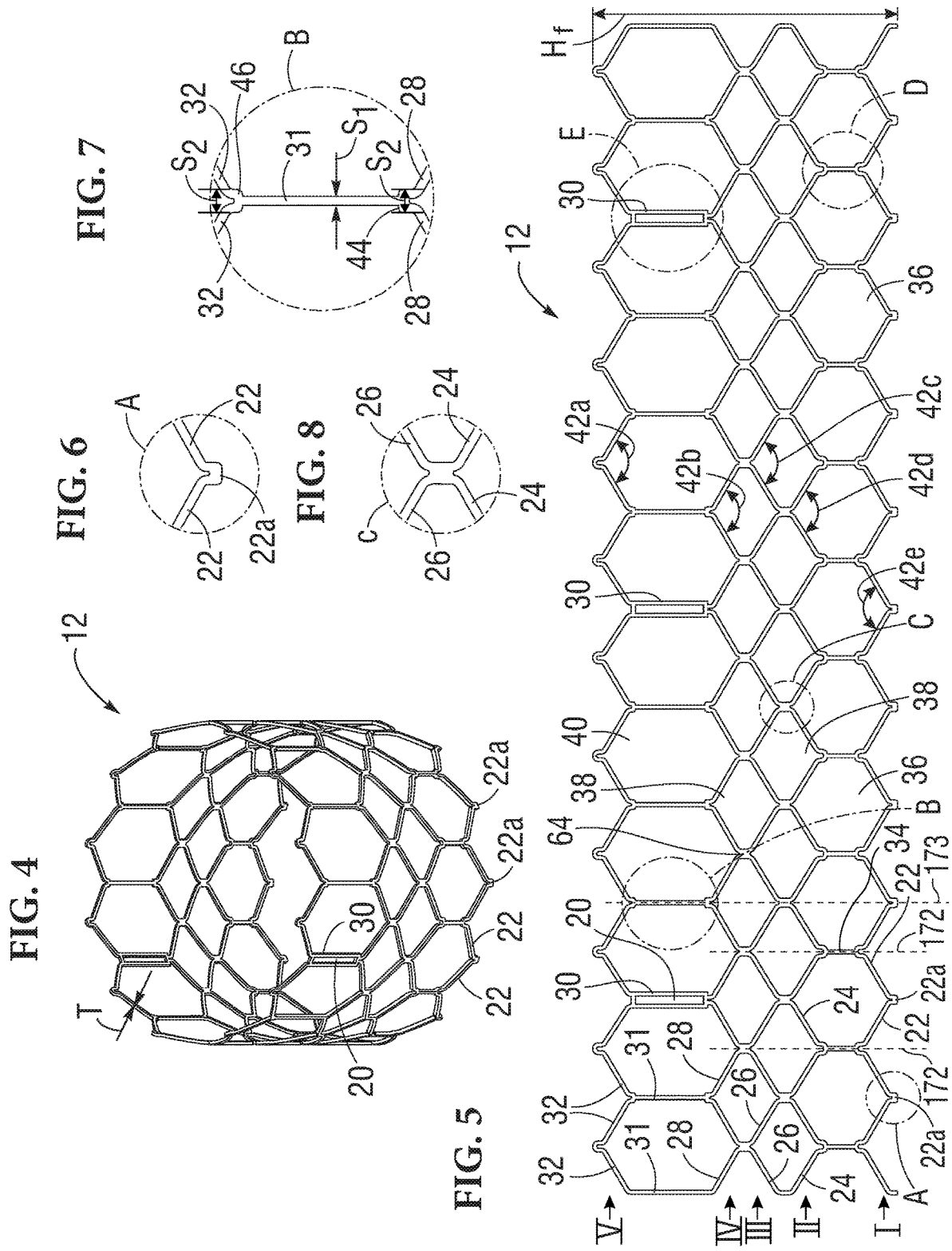

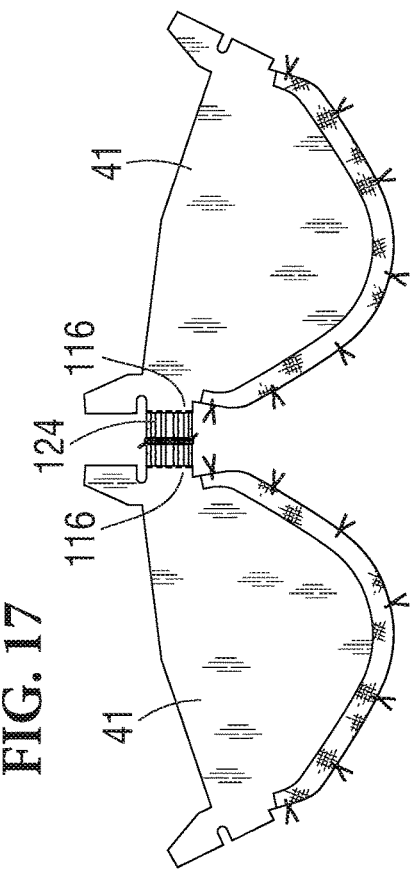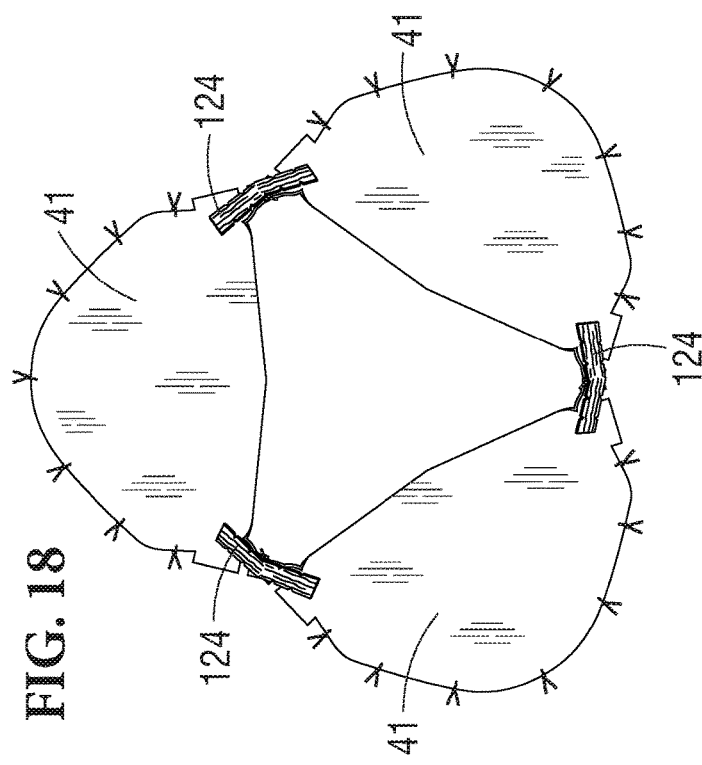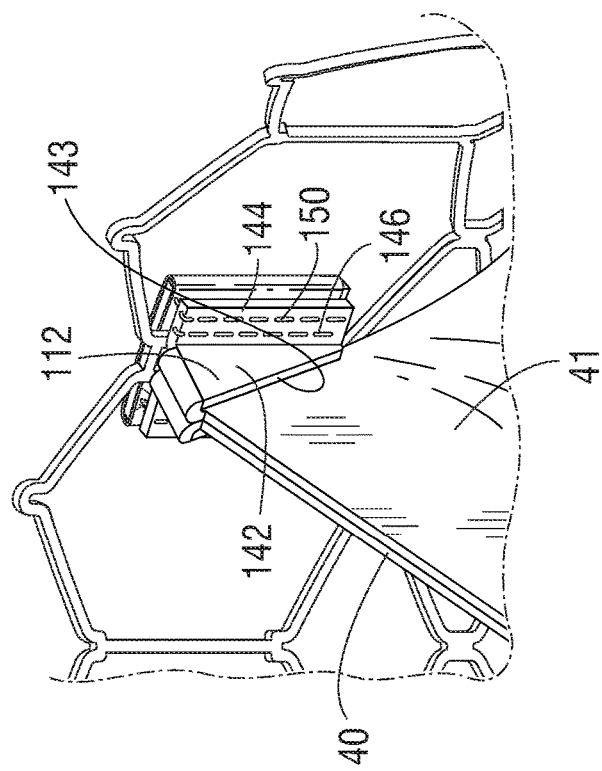

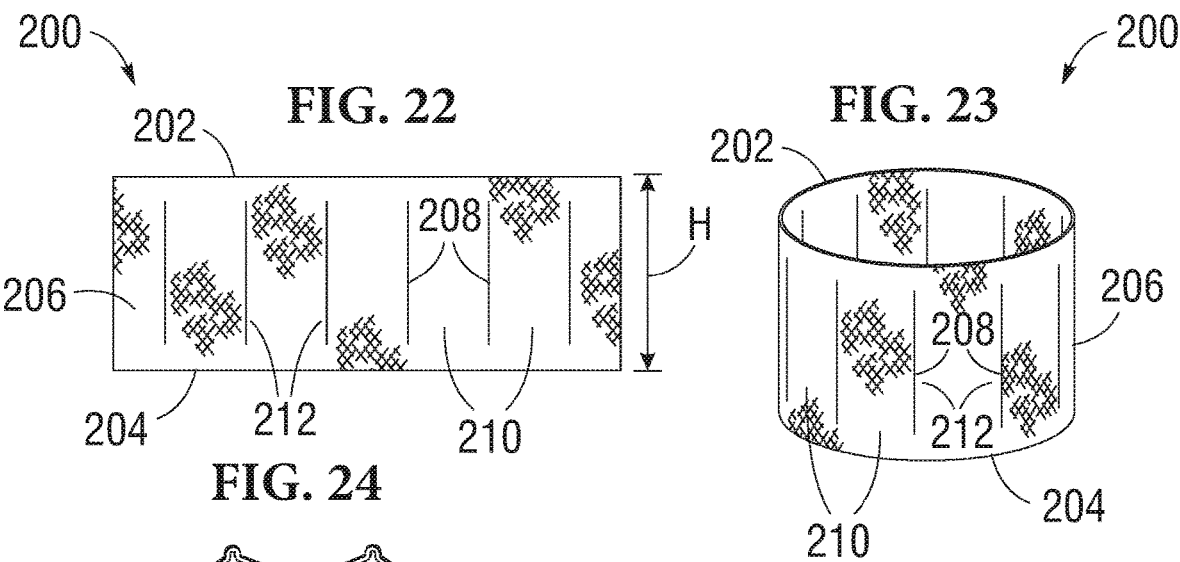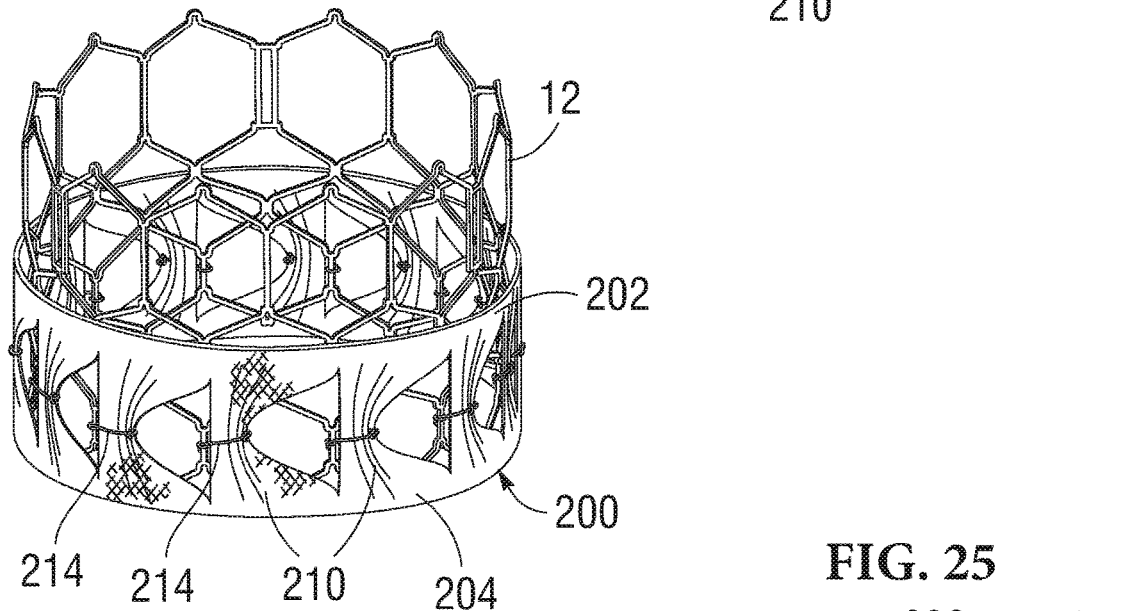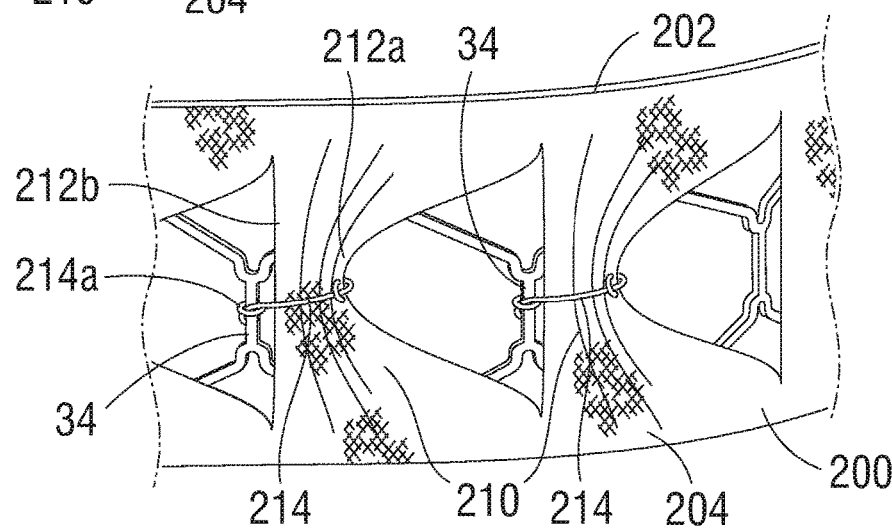

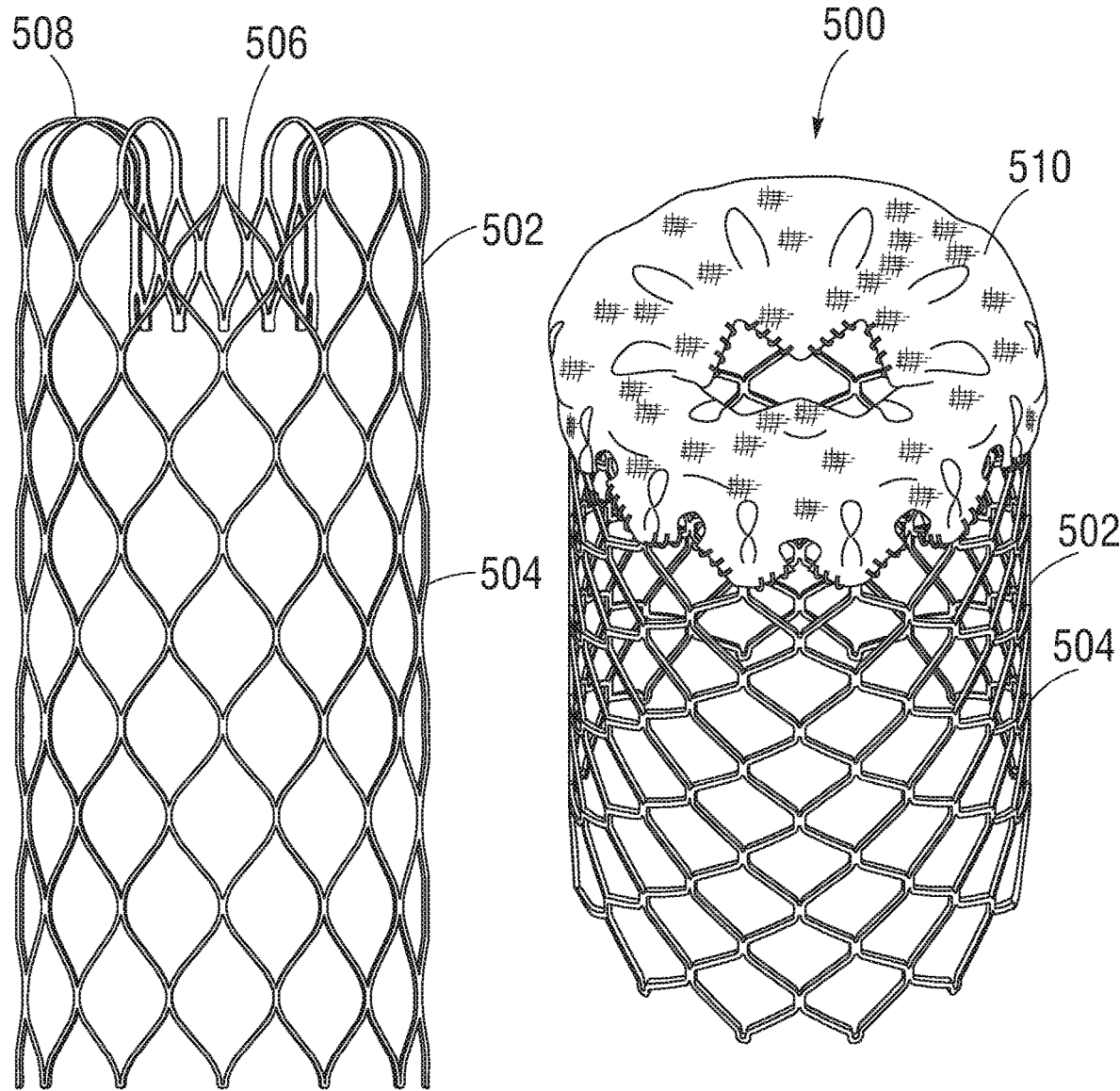

SEALING MEMBER FOR PROSTHETIC HEART VALVE

CROSS REFERENCE TO RELATED APPLICATION

This application is a divisional of U.S. application Ser. No. 16/103,985, filed Aug. 16, 2018, which claims the benefit of U.S. Provisional Application Ser. No. 62/548,280, filed on Aug. 21, 2017, which applications are incorporated by reference herein.

FIELD

The present disclosure relates to implantable, expandable prosthetic devices and to methods and apparatuses for such prosthetic devices.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans. Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For example, collapsible transcatheter prosthetic heart valves can be crimped to a compressed state and percutaneously introduced in the compressed state on a catheter and expanded to a functional size at the desired position by balloon inflation or by utilization of a self-expanding frame or stent.

A prosthetic valve for use in such a procedure can include a radially collapsible and expandable frame to which leaflets of the prosthetic valve can be coupled, and which can be percutaneously introduced in a collapsed configuration on a catheter and expanded in the desired position by balloon inflation or by utilization of a self-expanding frame or stent. A challenge in catheter-implanted prosthetic valves is control of perivalvular leakage around the valve, which can occur for a period of time following initial implantation. An additional challenge includes the process of crimping such a prosthetic valve to a profile suitable for percutaneous delivery to a patient.

SUMMARY

Embodiments of a radially collapsible and expandable prosthetic valve are disclosed herein that include an improved outer skirt for reducing perivalvular leakage, as well as related methods and apparatuses including such prosthetic valves. In several embodiments, the disclosed prosthetic valves are configured as replacement heart valves for implantation into a patient.

In one representative embodiment, an implantable prosthetic heart valve can include an annular frame, a leaflet structure positioned within the frame and secured thereto, and an annular outer skirt positioned around an outer surface of the frame. The frame can include an inflow end and an outflow end and can be radially collapsible and expandable between a radially collapsed configuration and a radially expanded configuration. The frame can define an axial direction extending from the inflow end to the outflow end. The outer skirt can include an inflow edge portion secured to the frame at a first location, an outflow edge portion secured to the frame at a second location, an intermediate portion between the inflow edge portion and the outflow edge portion, and a plurality of tethers. The intermediate portion can include a plurality of circumferentially spaced, axially extending slits that define a plurality of skirt segments between each pair of slits, and each skirt segment can include first and second opposing edge portions. Each tether can be secured to the first edge portion of a skirt segment at a first end of the tether, can extend across the second edge portion of the same skirt segment, and can be secured to the frame or an adjacent skirt segment at a second end of the tether such that when the frame is expanded to the radially expanded configuration, the first edge portion is pulled in a circumferential direction toward the second portion by the tether.

In some embodiments, the second end of each tether can be secured to the frame.

In some embodiments, the second end of each tether can be secured to the frame at a location adjacent to the second edge portion of the skirt segment that the first end of the tether is secured to.

In some embodiments, the frame can include a plurality of struts and the second end of each tether can be secured to the frame at a strut adjacent to the second edge portion of the skirt segment that the first end of the tether is secured to.

In some embodiments, each tether can be positioned radially outside of the skirt segment.

In some embodiments, each tether can be positioned radially inside of the skirt segment.

In some embodiments, the tethers can comprise a first set of tethers positioned radially outside of the skirt segment and a second set of tethers positioned radially inside of the skirt segment.

In some embodiments, the tethers can comprise a plurality of first tethers and a plurality of second tethers. In such embodiments, each first tether can have a first end secured to the first edge portion of a respective skirt segment, can extend across the second edge portion of the same skirt segment, and can have a second end secured to the frame at a first location. In such embodiments, each second tether can have a first end secured to the second edge portion of a respective skirt segment, can extend across the first edge portion of the same skirt segment, and can have a second end secured to the frame at a second location. In such embodiments, the first and second locations can be adjacent opposite sides of the skirt segment such that when the frame is expanded to the radially expanded configuration, the second tether pulls the second edge portion toward the first edge portion and the first tether pulls the first edge portion toward the second edge portion.

In some embodiments, the first ethers can be positioned radially outside of the outer skirt and the second tethers can be positioned radially inside of the outer skirt.

In some embodiments, the first ethers and the second tethers can each be positioned radially outside of the outer skirt.

In some embodiments, the first tethers and the second tethers can each be positioned radially inside of the outer skirt.

In some embodiments, the second end of each tether can be secured to an adjacent skirt segment.

In some embodiments, the plurality of tethers can comprise a plurality of first tethers and a plurality of second tethers. In such embodiments, each skirt segment can be coupled to a first adjacent skirt segment by a respective first tether and a second adjacent skirt segment by a respective second tether, such that when the frame is expanded to the radially expanded configuration, the first and second tethers pull the first and second edge portions of the skirt segment toward each other.

In some embodiments, for each skirt segment, a first tether can extend from the first edge portion of the skirt segment across the second edge portion and can be secured to the first adjacent skirt segment, and a second tether can extend from the second edge portion of the skirt segment across the first edge portion, and can be secured to the second adjacent skirt segment.

In some embodiments, the plurality of first tethers can be positioned radially inside of the outer skirt and the plurality of second tethers can be positioned radially outside of the outer skirt.

In another representative embodiment, an implantable prosthetic valve can include an annular frame, a leaflet structure positioned within the frame and secured thereto, and an outer sealing member positioned around an outer surface of the frame. The frame can include an inflow end and an outflow end and can be radially collapsible and expandable between a radially collapsed configuration and a radially expanded configuration. The frame can define an axial direction extending from the inflow end to the outflow end. The outer sealing member can include a plurality of sealing segments. Each sealing segment can be coupled to the frame and/or another sealing segment by a tether that pulls a portion of the sealing segment in a circumferential direction when the frame is radially expanded to the expanded configuration.

In some embodiments, each sealing segment can have upper and lower portions connected to the frame at axially spaced apart locations on the frame that move toward each other upon radial expansion of the frame and cause a portion of the sealing segment to move radially outwardly away from the frame.

In some embodiments, a width of each sealing segment in a circumferential direction can be reduced by a pulling force of a tether connected to the sealing segment upon radial expansion of the frame.

In some embodiments, each sealing segment can become at least partially twisted by a pulling force of a tether connected to the sealing segment upon radial expansion of the frame.

In some embodiments, each tether can have one end secured to a sealing segment and another end secured to the frame or another sealing segment.

The foregoing and other objects, features, and advantages of the disclosure will become more apparent from the following detailed description, which proceeds with reference to the accompanying figures.

BRIEF DESCRIPTION OF THE DRAWINGS

FIGS. 1-3 show an exemplary embodiment of a prosthetic heart valve.

FIGS. 4-10 show an exemplary frame of the prosthetic heart valve of FIG. 1.

FIGS. 17-18 show the assembly of an exemplary leaflet structure.

FIG. 19 shows the assembly of commissure portions of the leaflet structure with window frame portions of the frame.

FIGS. 22-23 show various views of another exemplary outer skirt.

FIGS. 24-25 show an exemplary embodiment of a prosthetic heart valve frame using the outer skirt of FIGS. 22-23.

FIGS. 33-34 show an alternative embodiment of a docking device for a prosthetic valve.

DETAILED DESCRIPTION

Figure 9:
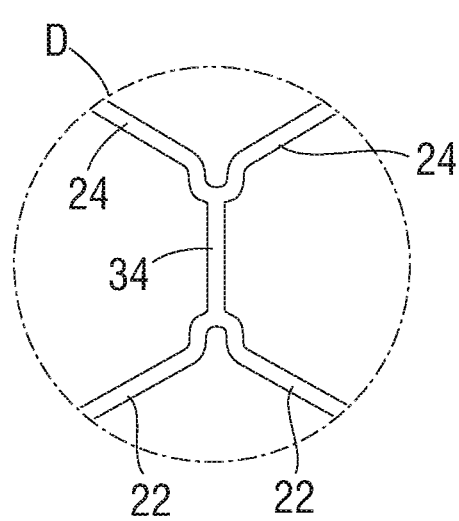
Figure 10:
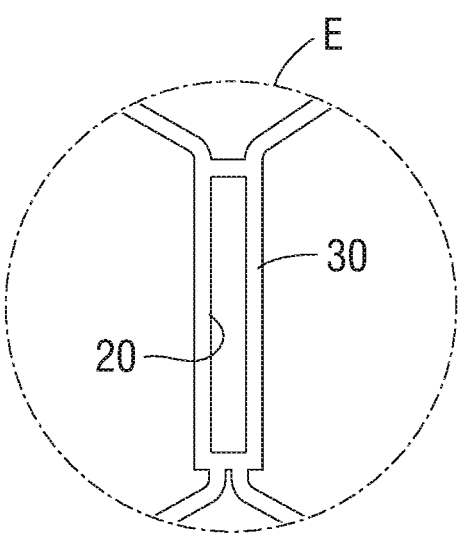
Figure 11:
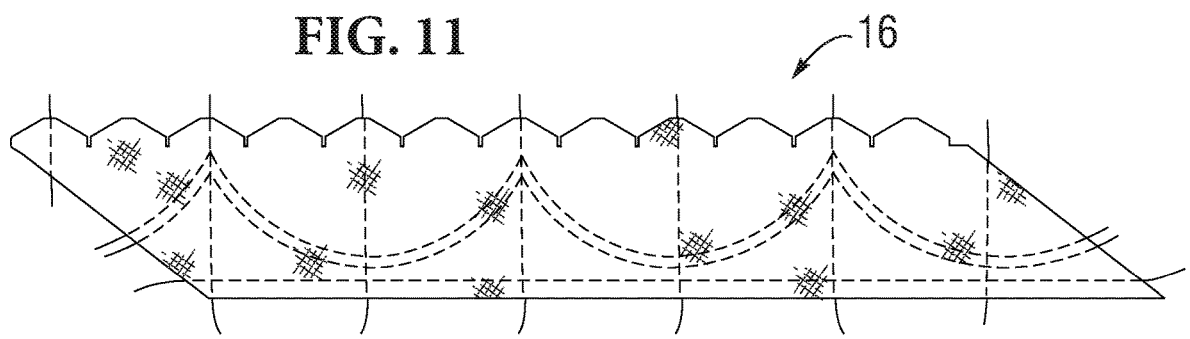
FIGS. 11-12 show an exemplary inner skirt of the prosthetic heart valve of FIG. 1.

FIGS. 1-3 show various views of a prosthetic heart valve 10, according to one embodiment. The illustrated prosthetic valve is adapted to be implanted in the native aortic annulus, although in other embodiments it can be adapted to be implanted in the other native annuluses of the heart (e.g., the pulmonary, mitral, and tricuspid valves). The prosthetic valve can also be adapted to be implanted in other tubular organs or passageways in the body. The prosthetic valve 10 can have four main components: a stent or frame 12, a valvular structure 14, an inner skirt 16, and a perivalvular sealing means or sealing member. The prosthetic valve 10 can have an inflow end portion 15, an intermediate portion 17, and an outflow end portion 19. In the illustrated embodiment, the perivalvular sealing means comprises an outer skirt 18 (which can also be referred to as an outer sealing member).

The valvular structure 14 can comprise three leaflets 41, collectively forming a leaflet structure, which can be arranged to collapse in a tricuspid arrangement, as best shown in FIG. 2. The lower edge of leaflet structure 14 desirably has an undulating, curved scalloped shape (suture line 154 shown in FIG. 21 tracks the scalloped shape of the leaflet structure). By forming the leaflets with this scalloped geometry, stresses on the leaflets are reduced, which in turn improves durability of the prosthetic valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the prosthetic valve. The leaflets 41 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference in its entirety herein.

The bare frame 12 is shown in FIG. 4. The frame 12 can be formed with a plurality of circumferentially spaced slots, or commissure windows, 20 (three in the illustrated embodiment) that are adapted to connect the commissures of the valvular structure 14 to the frame, as described in greater detail below. The frame 12 can be made of any of various suitable plastically-expandable materials (e.g., stainless steel, etc.) or self-expanding materials (e.g., nickel titanium alloy (NiTi), such as nitinol). When constructed of a plastically-expandable material, the frame 12 (and thus the prosthetic valve 10) can be crimped to a radially collapsed configuration on a delivery catheter and then expanded inside a patient by an inflatable balloon or equivalent expansion mechanism. When constructed of a self-expandable material, the frame 12 (and thus the prosthetic valve 10) can be crimped to a radially collapsed configuration and restrained in the collapsed configuration by insertion into a sheath or equivalent mechanism of a delivery catheter. Once inside the body, the prosthetic valve can be advanced from the delivery sheath, which allows the prosthetic valve to expand to its functional size.

Suitable plastically-expandable materials that can be used to form the frame 12 include, without limitation, stainless steel, a biocompatible, high-strength alloys (e.g., a cobalt-chromium or a nickel-cobalt-chromium alloys), polymers, or combinations thereof. In particular embodiments, frame 12 is made of a nickel-cobalt-chromium-molybdenum alloy, such as MP35N® alloy (SPS Technologies, Jenkintown, Pennsylvania), which is equivalent to UNS R30035 alloy (covered by ASTM F562-02). MP35N® alloy/UNS R30035 alloy comprises 35% nickel, 35% cobalt, 20% chromium, and 10% molybdenum, by weight. When MP35N® alloy is used as the frame material, as compared to stainless steel, less material is needed to achieve the same or better performance in radial and crush force resistance, fatigue resistances, and corrosion resistance. Moreover, since less material is required, the crimped profile of the frame can be reduced, thereby providing a lower profile prosthetic valve assembly for percutaneous delivery to the treatment location in the body.

Referring to FIGS. 4 and 5, the frame 12 in the illustrated embodiment comprises a first, lower row I of angled struts 22 arranged end-to-end and extending circumferentially at the inflow end of the frame; a second row II of circumferentially extending, angled struts 24; a third row III of circumferentially extending, angled struts 26; a fourth row IV of circumferentially extending, angled struts 28; and a fifth row V of circumferentially extending, angled struts 32 at the outflow end of the frame. A plurality of substantially straight axially extending struts 34 can be used to interconnect the struts 22 of the first row I with the struts 24 of the second row II. The fifth row V of angled struts 32 are connected to the fourth row IV of angled struts 28 by a plurality of axially extending window frame portions 30 (which define the commissure windows 20) and a plurality of axially extending struts 31. Each axial strut 31 and each frame portion 30 extends from a location defined by the convergence of the lower ends of two angled struts 32 to another location defined by the convergence of the upper ends of two angled struts 28. FIGS. 6, 7, 8, 9, and 10 are enlarged views of the portions of the frame 12 identified by letters A, B, C, D, and E, respectively, in FIG. 5.

Each commissure window frame portion 30 connects to a respective commissure of the leaflet structure 14. As can be seen each frame portion 30 is secured at its upper and lower ends to the adjacent rows of struts to provide a robust configuration that enhances fatigue resistance under cyclic loading of the prosthetic valve compared to cantilevered struts for supporting the commissures of the leaflet structure. This configuration enables a reduction in the frame wall thickness to achieve a smaller crimped diameter of the prosthetic valve. In particular embodiments, the thickness T of the frame 12 (FIG. 4) measured between the inner diameter and outer diameter is about 0.48 mm or less.

The struts and frame portions of the frame collectively define a plurality of open cells of the frame. At the inflow end of the frame 12, struts 22, struts 24, and struts 34 define a lower row of cells defining openings 36. The second, third, and fourth rows of struts 24, 26, and 28 define two intermediate rows of cells defining openings 38. The fourth and fifth rows of struts 28 and 32, along with frame portions 30 and struts 31, define an upper row of cells defining openings 40. The openings 40 are relatively large and are sized to allow portions of the leaflet structure 14 to protrude, or bulge, into and/or through the openings 40 when the frame 12 is crimped in order to minimize the crimping profile.

Figure 13:
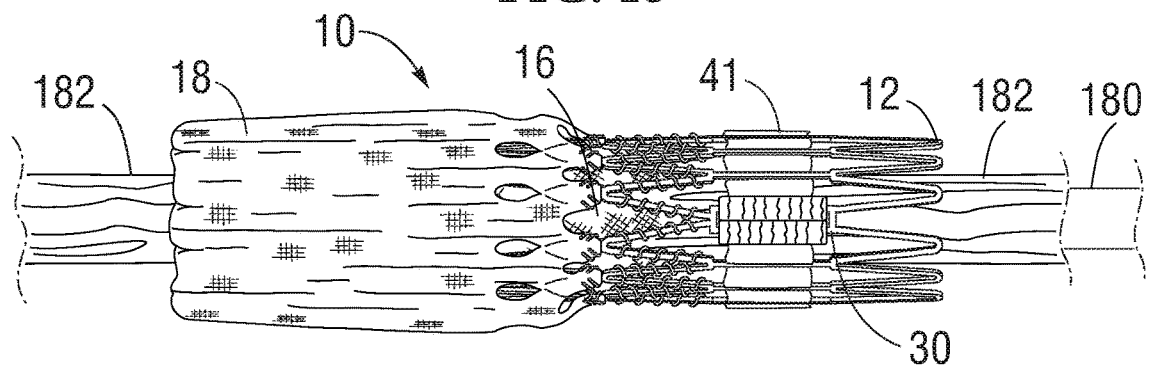
FIG. 13 shows the prosthetic heart valve of FIG. 1 in a collapsed configuration and mounted on an exemplary balloon catheter.

As best shown in FIG. 7, the lower end of the strut 31 is connected to two struts 28 at a node or junction 44, and the upper end of the strut 31 is connected to two struts 32 at a node or junction 46. The strut 31 can have a thickness S1 that is less than the thicknesses S2 of the junctions 44, 46. The junctions 44, 46, along with junctions 64, prevent full closure of openings 40. FIG. 13 shows the prosthetic valve 10 crimped on a balloon catheter. As can be seen, the geometry of the struts 31, and junctions 44, 46, and 64 assists in creating enough space in openings 40 in the collapsed configuration to allow portions of the prosthetic leaflets to protrude or bulge outwardly through openings. This allows the prosthetic valve to be crimped to a relatively smaller diameter than if all of the leaflet material were constrained within the crimped frame.

The frame 12 is configured to reduce, to prevent, or to minimize possible over-expansion of the prosthetic valve at a predetermined balloon pressure, especially at the outflow end portion of the frame, which supports the leaflet structure 14. In one aspect, the frame is configured to have relatively larger angles 42a, 42b, 42c, 42d, 42e between struts, as shown in FIG. 5. The larger the angle, the greater the force required to open (expand) the frame. As such, the angles between the struts of the frame can be selected to limit radial expansion of the frame at a given opening pressure (e.g., inflation pressure of the balloon). In particular embodiments, these angles are at least 110 degrees or greater when the frame is expanded to its functional size, and even more particularly these angles are up to about 120 degrees when the frame is expanded to its functional size.

In addition, the inflow and outflow ends of a frame generally tend to over-expand more so than the middle portion of the frame due to the "dog-boning" effect of the balloon used to expand the prosthetic valve. To protect against over-expansion of the leaflet structure 14, the leaflet structure desirably is secured to the frame 12 below the upper row of struts 32, as best shown in FIG. 1. Thus, in the event that the outflow end of the frame is over-expanded, the leaflet structure is positioned at a level below where over-expansion is likely to occur, thereby protecting the leaflet structure from over-expansion.

In one type of prosthetic valve construction, portions of the leaflets protrude longitudinally beyond the outflow end of the frame when the prosthetic valve is crimped if the leaflets are connected too close to the distal end of the frame. If the delivery catheter on which the crimped prosthetic valve is mounted includes a pushing mechanism or stop member that pushes against or abuts the outflow end of the prosthetic valve (for example, to maintain the position of the crimped prosthetic valve on the delivery catheter), the pushing member or stop member can damage the portions of the exposed leaflets that extend beyond the outflow end of the frame. Another benefit of connecting the leaflets at a location spaced away from the outflow end of the frame is that when the prosthetic valve is crimped on a delivery catheter, the outflow end of the frame 12 rather than the leaflets 41 is the proximal-most component of the prosthetic valve 10. As such, if the delivery catheter includes a pushing mechanism or stop member that pushes against or abuts the outflow end of the prosthetic valve, the pushing mechanism or stop member contacts the outflow end of the frame, and not leaflets 41, so as to avoid damage to the leaflets.

Also, as can be seen in FIG. 5, the openings 36 of the lowermost row of openings in the frame are relatively larger than the openings 38 of the two intermediate rows of openings. This allows the frame, when crimped, to assume an overall tapered shape that tapers from a maximum diameter at the outflow end of the prosthetic valve to a minimum diameter at the inflow end of the prosthetic valve. When crimped, the frame 12 can have a reduced diameter region extending along a portion of the frame adjacent the inflow end of the frame that generally corresponds to the region of the frame covered by the outer skirt 18. In some embodiments, the reduced diameter region is reduced compared to the diameter of the upper portion of the frame (which is not covered by the outer skirt) such that the outer skirt 18 does not increase the overall crimp profile of the prosthetic valve. When the prosthetic valve is deployed, the frame can expand to the generally cylindrical shape shown in FIG. 4. In one example, the frame of a 26-mm prosthetic valve, when crimped, had a first diameter of 14 French at the outflow end of the prosthetic valve and a second diameter of 12 French at the inflow end of the prosthetic valve.

The main functions of the inner skirt 16 are to assist in securing the valvular structure 14 to the frame 12 and to assist in forming a good seal between the prosthetic valve and the native annulus by blocking the flow of blood through the open cells of the frame 12 below the lower edge of the leaflets. The inner skirt 16 desirably comprises a tough, tear resistant material such as polyethylene terephthalate (PET), although various other synthetic materials or natural materials (e.g., pericardial tissue) can be used. The thickness of the skirt desirably is less than about 0.15 mm (about 6 mil), and desirably less than about 0.1 mm (about 4 mil), and even more desirably about 0.05 mm (about 2 mil). In particular embodiments, the skirt 16 can have a variable thickness, for example, the skirt can be thicker at least one of its edges than at its center. In one implementation, the skirt 16 can comprise a PET skirt having a thickness of about 0.07 mm at its edges and about 0.06 mm at its center. The thinner skirt can provide for better crimping performances while still providing good sealing.

Figure 20:
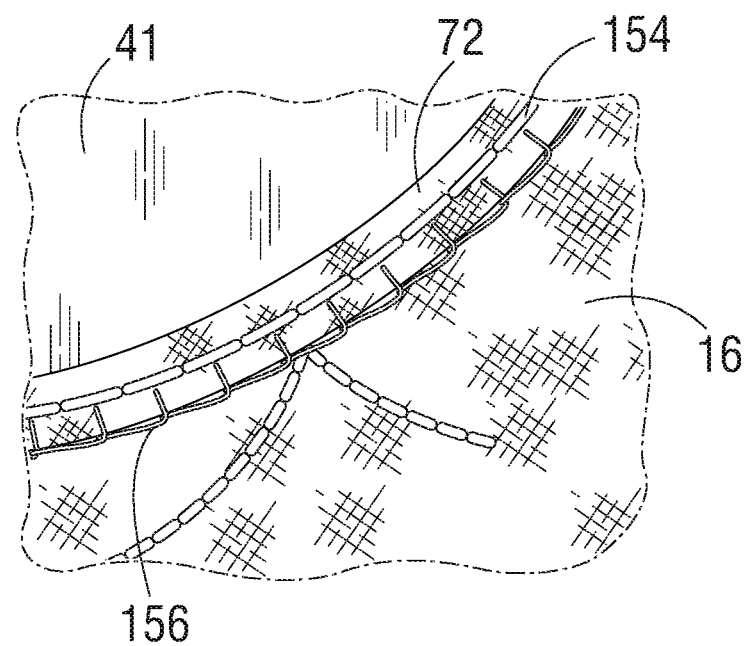
FIGS. 20-21 show the assembly of the leaflet structure with the inner skirt along a lower edge of the leaflets.
Figure 21:
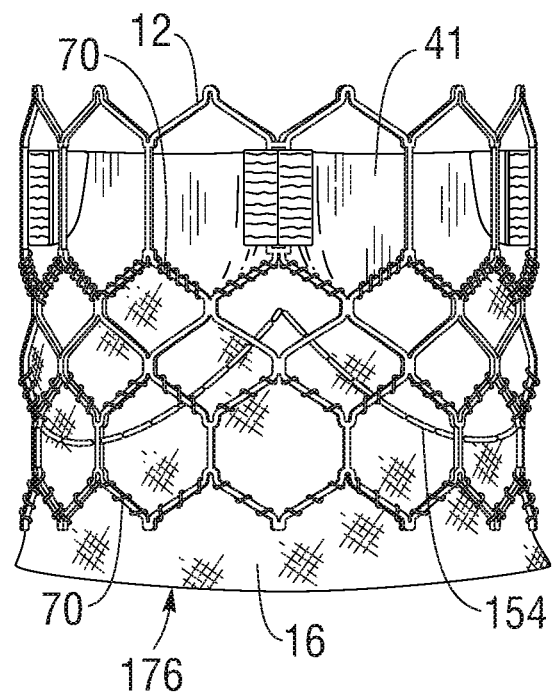

The skirt 16 can be secured to the inside of frame 12 via sutures 70, as shown in FIG. 21. Valvular structure 14 can be attached to the skirt via one or more reinforcing strips 72 (which collectively can form a sleeve), for example thin, PET reinforcing strips, discussed below, which enables a secure suturing and protects the pericardial tissue of the leaflet structure from tears. Valvular structure 14 can be sandwiched between skirt 16 and the thin PET strips 72 as shown in FIG. 20. Sutures 154, which secure the PET strip and the leaflet structure 14 to skirt 16, can be any suitable suture, such as Ethibond Excel® PET suture (Johnson & Johnson, New Brunswick, New Jersey). Sutures 154 desirably track the curvature of the bottom edge of leaflet structure 14, as described in more detail below.

Some fabric skirts comprise a weave of warp and weft fibers that extend perpendicularly to each other and with one set of the fibers extending longitudinally between the upper and lower edges of the skirt. When the metal frame to which such a fabric skirt is secured is radially compressed, the overall axial length of the frame increases. However, a fabric skirt with limited elasticity cannot elongate along with the frame and therefore tends to deform the struts of the frame and to prevent uniform crimping.

Figure 12:
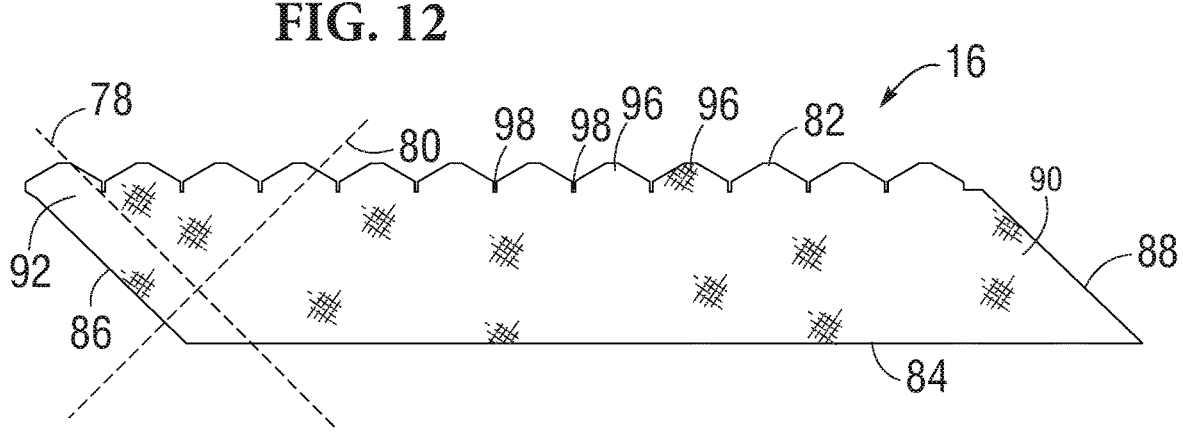

Referring to FIG. 12, in one embodiment, the skirt 16 desirably is woven from a first set of fibers, or yarns or strands, 78 and a second set of fibers, or yarns or strands, 80, both of which are non-perpendicular to the upper edge 82 and the lower edge 84 of the skirt. In particular embodiments, the first set of fibers 78 and the second set of fibers 80 extend at angles of about 45 degrees (e.g., 15-75 degrees or 30-60 degrees) relative to the upper and lower edges 82, 84. For example, the skirt 16 can be formed by weaving the fibers at 45 degree angles relative to the upper and lower edges of the fabric. Alternatively, the skirt 16 can be diagonally cut (cut on a bias) from a vertically woven fabric (where the fibers extend perpendicularly to the edges of the material) such that the fibers extend at 45 degree angles relative to the cut upper and lower edges of the skirt. As further shown in FIG. 12, the opposing short edges 86, 88 of the skirt desirably are non-perpendicular to the upper and lower edges 82, 84. For example, the short edges 86, 88 desirably extend at angles of about 45 degrees relative to the upper and lower edges and therefore are aligned with the first set of fibers 78. Therefore the overall general shape of the skirt can be that of a rhomboid or parallelogram.

Figure 14:
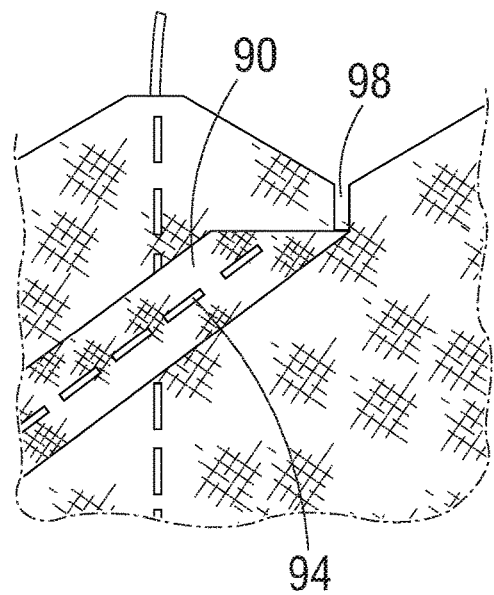
FIGS. 14-16 show the assembly of the inner skirt of FIG. 11 with the frame of FIG. 4.
Figure 15:
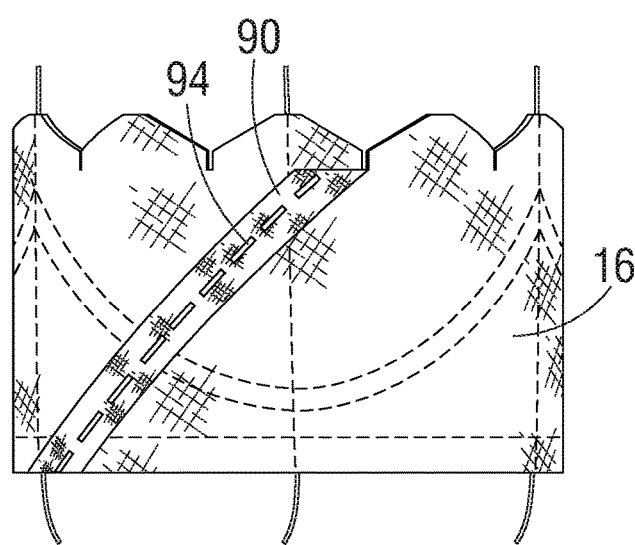
Figure 16:
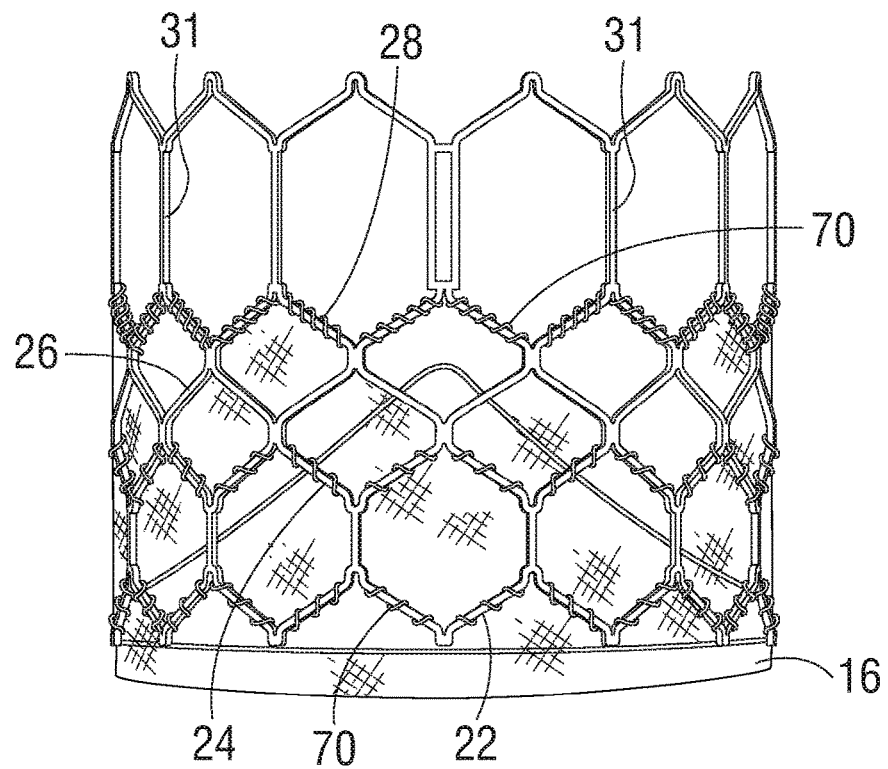

FIGS. 14 and 15 show the inner skirt 16 after opposing short edge portions 90, 92 have been sewn together to form the annular shape of the skirt. As shown, the edge portion 90 can be placed in an overlapping relationship relative to the opposite edge portion 92, and the two edge portions can be sewn together with a diagonally extending suture line 94 that is parallel to short edges 86, 88. The upper edge portion of the inner skirt 16 can be formed with a plurality of projections 96 that define an undulating shape that generally follows the shape or contour of the fourth row of struts 28 immediately adjacent the lower ends of axial struts 31. In this manner, as best shown in FIG. 16, the upper edge of the inner skirt 16 can be tightly secured to struts 28 with sutures 70. The inner skirt 16 can also be formed with slits 98 to facilitate attachment of the skirt to the frame. Slits 98 can be dimensioned so as to allow an upper edge portion of the inner skirt 16 to be partially wrapped around struts 28 and to reduce stresses in the skirt during the attachment procedure. For example, in the illustrated embodiment, the inner skirt 16 is placed on the inside of frame 12 and an upper edge portion of the skirt is wrapped around the upper surfaces of struts 28 and secured in place with sutures 70. Wrapping the upper edge portion of the inner skirt 16 around struts 28 in this manner provides for a stronger and more durable attachment of the skirt to the frame. The inner skirt 16 can also be secured to the first, second, and/or third rows of struts 22, 24, and 26, respectively, with sutures 70.

Referring again to FIG. 12, due to the angled orientation of the fibers relative to the upper and lower edges in this embodiment, the skirt can undergo greater elongation in the axial direction (i.e., in a direction from the upper edge 82 to the lower edge 84).

Thus, when the metal frame 12 is crimped (as shown in FIG. 13), the inner skirt 16 can elongate in the axial direction along with the frame and therefore provide a more uniform and predictable crimping profile. Each cell of the metal frame in the illustrated embodiment includes at least four angled struts that rotate towards the axial direction on crimping (e.g., the angled struts become more aligned with the length of the frame). The angled struts of each cell function as a mechanism for rotating the fibers of the skirt in the same direction of the struts, allowing the skirt to elongate along the length of the struts. This allows for greater elongation of the skirt and avoids undesirable deformation of the struts when the prosthetic valve is crimped.

In addition, the spacing between the woven fibers or yarns can be increased to facilitate elongation of the skirt in the axial direction. For example, for a PET inner skirt 16 formed from 20-denier yarn, the yarn density can be about 15% to about 30% lower than in a typical PET skirt. In some examples, the yarn spacing of the inner skirt 16 can be from about 60 yarns per cm (about 155 yarns per inch) to about 70 yarns per cm (about 180 yarns per inch), such as about 63 yarns per cm (about 160 yarns per inch), whereas in a typical PET skirt the yarn spacing can be from about 85 yarns per cm (about 217 yarns per inch) to about 97 yarns per cm (about 247 yarns per inch). The oblique edges 86, 88 promote a uniform and even distribution of the fabric material along inner circumference of the frame during crimping so as to facilitate uniform crimping to the smallest possible diameter. Additionally, cutting diagonal sutures in a vertical manner may leave loose fringes along the cut edges. The oblique edges 86, 88 help minimize this from occurring.

In alternative embodiments, the skirt can be formed from woven elastic fibers that can stretch in the axial direction during crimping of the prosthetic valve. The warp and weft fibers can run perpendicularly and parallel to the upper and lower edges of the skirt, or alternatively, they can extend at angles between 0 and 90 degrees relative to the upper and lower edges of the skirt, as described above.

The inner skirt 16 can be sutured to the frame 12 at locations away from the suture line 154 so that the skirt can be more pliable in that area. This configuration can avoid stress concentrations at the suture line 154, which attaches the lower edges of the leaflets to the inner skirt 16.

As noted above, the leaflet structure 14 in the illustrated embodiment includes three flexible leaflets 41 (although a greater or a smaller number of leaflets can be used). Additional information regarding the leaflets, as well as additional information regarding skirt material, can be found, for example, in U.S. patent application Ser. No. 14/704,861, filed May 5, 2015, which is incorporated by reference in its entirety.

The leaflets 41 can be secured to one another at their adjacent sides to form commissures 122 of the leaflet structure. A plurality of flexible connectors 124 (one of which is shown in FIG. 17) can be used to interconnect pairs of adjacent sides of the leaflets and to connect the leaflets to the commissure window frame portions 30 (FIG. 5).

FIG. 17 shows the adjacent sides of two leaflets 41 interconnected by a flexible connector 124. Three leaflets 41 can be secured to each other side-to-side using three flexible connectors 124, as shown in FIG. 18. Additional information regarding connecting the leaflets to each other, as well as connecting the leaflets to the frame, can be found, for example, in U.S. Patent Application Publication No. 2012/0123529, which is incorporated by reference herein in its entirety.

As noted above, the inner skirt 16 can be used to assist in suturing the leaflet structure 14 to the frame. The inner skirt 16 can have an undulating temporary marking suture to guide the attachment of the lower edges of each leaflet 41. The inner skirt 16 itself can be sutured to the struts of the frame 12 using sutures 70, as noted above, before securing the leaflet structure 14 to the skirt 16. The struts that intersect the marking suture desirably are not attached to the inner skirt 16. This allows the inner skirt 16 to be more pliable in the areas not secured to the frame and minimizes stress concentrations along the suture line that secures the lower edges of the leaflets to the skirt. As noted above, when the skirt is secured to the frame, the fibers 78, 80 of the skirt (see FIG. 12) generally align with the angled struts of the frame to promote uniform crimping and expansion of the frame.

FIG. 19 shows one specific approach for securing the commissure portions 122 of the leaflet structure 14 to the commissure window frame portions 30 of the frame. In this approach, the flexible connector 124 (FIG. 18) securing two adjacent sides of two leaflets is folded widthwise and the upper tab portions 112 are folded downwardly against the flexible connector. Each upper tab portion 112 is creased lengthwise (vertically) to assume an L-shape having an inner portion 142 folded against the inner surface of the leaflet and an outer portion 144 folded against the connector 124. The outer portion 144 can then be sutured to the connector 124 along a suture line 146. Next, the commissure tab assembly is inserted through the commissure window 20 of a corresponding window frame portion 30, and the folds outside of the window frame portion 30 can be sutured to portions 144.

FIG. 19 also shows that the folded down upper tab portions 112 can form a double layer of leaflet material at the commissures. The inner portions 142 of the upper tab portions 112 are positioned flat against layers of the two leaflets 41 forming the commissures, such that each commissure comprises four layers of leaflet material just inside of the window frames 30. This four-layered portion of the commissures can be more resistant to bending, or articulating, than the portion of the leaflets 41 just radially inward from the relatively more-rigid four-layered portion. This causes the leaflets 41 to articulate primarily at inner edges 143 of the folded-down inner portions 142 in response to blood flowing through the prosthetic valve during operation within the body, as opposed to articulating about or proximal to the axial struts of the window frames 30. Because the leaflets articulate at a location spaced radially inwardly from the window frames 30, the leaflets can avoid contact with and damage from the frame. However, under high forces, the four layered portion of the commissures can splay apart about a longitudinal axis adjacent to the window frame 30, with each inner portion 142 folding out against the respective outer portion 144. For example, this can occur when the prosthetic valve 10 is compressed and mounted onto a delivery shaft, allowing for a smaller crimped diameter. The four-layered portion of the commissures can also splay apart about the longitudinal axis when the balloon catheter is inflated during expansion of the prosthetic valve, which can relieve some of the pressure on the commissures caused by the balloon, reducing potential damage to the commissures during expansion.

After all three commissure tab assemblies are secured to respective window frame portions 30, the lower edges of the leaflets 41 between the commissure tab assemblies can be sutured to the inner skirt 16. For example, as shown in FIG. 20, each leaflet 41 can be sutured to the inner skirt 16 along suture line 154 using, for example, Ethibond Excel® PET thread. The sutures can be in-and-out sutures extending through each leaflet 41, the inner skirt 16, and each reinforcing strip 72. Each leaflet 41 and respective reinforcing strip 72 can be sewn separately to the inner skirt 16. In this manner, the lower edges of the leaflets are secured to the frame 12 via the inner skirt 16. As shown in FIG. 20, the leaflets can be further secured to the skirt with blanket sutures 156 that extend through each reinforcing strip 72, leaflet 41 and the inner skirt 16 while looping around the edges of the reinforcing strips 72 and leaflets 41. The blanket sutures 156 can be formed from PTFE suture material. FIG. 21 shows a side view of the frame 12, leaflet structure 14 and the inner skirt 16 after securing the leaflet structure 14 and the inner skirt 16 to the frame 12 and the leaflet structure 14 to the inner skirt 16.

FIGS. 22-23 show another embodiment of an outer skirt or sealing member 200 that can be incorporated in a prosthetic valve, such as valve 10. FIG. 22 shows a flattened view of the outer skirt 200 prior to its attachment to a prosthetic heart valve. FIG. 23 shows a view of the outer skirt 200 in a cylindrical configuration prior to its attachment to a prosthetic heart valve.

Referring to FIGS. 22-23, the outer skirt 200 can comprise an upper edge portion 202, a lower edge portion 204 and an intermediate portion 206 disposed between the upper edge portion 202 and the lower edge portion 204. The intermediate portion 206 can comprise a plurality of vertical slits, cuts, or openings 208 cut or otherwise formed in the outer skirt 200 at circumferentially spaced apart locations. Each adjacent pair of slits 208 defines a vertical strip 210 (also referred to as a skirt segment) therebetween such that there are a plurality of such strips 210, each extending lengthwise along the length of the outer skirt 200 from the upper edge portion 202 to the lower edge portion 204. Each strip 210 in the illustrated embodiment defines opposing longitudinally extending edge portions 212 adjacent to respective slits 208.

The outer skirt 200 can be formed from synthetic materials, including woven fabrics, non-woven fabrics, or non-fabric materials (e.g., foams, sheets), formed from any of various suitable biocompatible polymer, such as PET, PTFE, ePTFE, polyurethane, polyester; natural tissue (pericardium); and/or other suitable materials configured to restrict and/or prevent blood-flow therethrough. Alternatively, the outer skirt 200 can be formed from an elastic material. The slits 208 can be laser cut or formed by any other suitable means. The outer skirt 200 can be secured to the frame of a prosthetic heart valve as discussed below in connection with FIGS. 24-25.

The slits 208 in the illustrated embodiment are straight, and therefore define strips 210 that are rectangular. However, in other embodiments, the slits 208 can have various other shapes, including curved portions, so as to define strips 210 of various shapes. For example, the slits 208 can have an undulating or sinusoidal shape so as to define strips 210 having longitudinal side edges of the same shape. Further, as shown in the illustrated embodiment, the slits 208 terminate short of the upper and lower edges of the skirt. As such, the strips 210 are connected to each other at their upper and lower ends by the upper edge portion 202 and the lower edge portion 204 of the skirt. In other embodiments, one or more of the slits 208 can extend all the way to the very upper or lower edge of the skirt such that a strip 210 is not connected to an adjacent strip where the slit 208 extends all the way to an upper or lower edge of the skirt.

FIGS. 24-25 show the outer skirt 200 of FIGS. 22-23 mounted on the outside of a frame 12. FIG. 25 shows an enlarged view of a portion of the frame 12 and the outer skirt 200. The frame 12 and the outer skirt 200 can be part of a prosthetic heart valve similar to prosthetic heart valve 10 that can include a valvular structure similar to valvular structure 14 and an inner skirt similar to inner skirt 16, as best shown in FIGS. 1-3. For illustrative purposes, FIGS. 24-25 only show the frame 12 and the outer skirt 200.

As previously described and as best shown in FIG. 5, the frame 12 comprises axially extending struts 34 between rows I and II of angled struts 22, 24. The first row of struts I, the second row of struts II and the axially extending struts 34 define a plurality of cells defining openings 36. Prior to attachment to the frame 12, the outer skirt 200 can be arranged around the outer surface of the frame 12 such that each slit 208 is adjacent to an axially extending strut 34 and such that each strip 210 substantially covers one of the cell openings 36. The upper and lower edge portions 202, 204 of the outer skirt 200 can be secured to the frame 212 using suitable techniques and/or mechanisms, including sutures, an adhesive and/or ultrasonic welding. In particular embodiments, for example, the entire extent of the lower edge portion 204 can be sutured to the angled struts 22 of row I of the frame 12, while the upper edge portion 202 can be sutured at the junctions formed by the intersection of struts 26 with struts 28. In other embodiments, the entire extent of the upper edge portion 202 can be sutured to struts 26 or struts 28. In some embodiments, the upper edge portion 202 can have an undulating or scalloped shaped, such as shown for the skirt 18 and can be sutured to the frame 12 as shown in FIG. 1.

In particular embodiments, the height H of the outer skirt 200 in the axial direction can be greater than the axial distance between the attachment locations of the upper and lower edge portions 202, 204 of the outer skirt 200 when the frame 12 is in a radially collapsed configuration. In this manner, radial expansion of the frame 12 results in foreshortening of the frame 12 between the attachment locations of the skirt 200, creating slack in the skirt 200 between the attachments locations and allowing the strips 210 to move outwardly from the frame 12. In the illustrated example, the axial length of the outer skirt 200 is equal to the length of a strut 22 plus the length of a strut 34 plus the length of a strut 24 plus the length of a strut 26 of frame 12. In alternative embodiments, the outer skirt 200 can have different heights H, depending on the particular application.

In addition to the upper and lower end portions 202, 204 being secured to the frame 12, at least one of the longitudinal edge portions 212 of each of the plurality of strips 210 can be secured to the frame 12 and/or to other strips so as to produce circumferential and/or twisting movement of the strips 210 upon radial expansion of the frame 12. In the illustrated example, the strips 210 are secured to the frame 12 with tethers 214, which can be, for example, sutures, flexible wires, filaments, or similar materials. Alternatively, the strips 210 can be secured to the frame 12 with adhesive and/or ultrasonic welding in addition to or in lieu of sutures.

In the illustrated embodiment, for each one of the plurality of strips 210, an edge portion 212a can be secured to a strut 34 with a tether 214 having one end 214a tied off or knotted around the strut 34 and the other end 214b tied off to the strip 212. Desirably, the edge 212a of the strip 210 is secured to the strut 34 that is closest to the unsecured edge 212b of the same strip such that the tether 214 extends across the width of the strip 210 and the unsecured edge 212b. As such, when the frame 12 is in a radially collapsed configuration, the axially extending struts 34 are closer together and the strips 210 extend in a substantially straight line between the upper and lower edges 202, 204 of the skirt 200. However, when the frame 12 expands to a radially expanded configuration, the axially extending struts 34 move away from each other, pulling the secured edge 212a of each strip 210 toward its unsecured edge 212b, thereby decreasing the width of the strip 210 between its upper and lower ends (the width of the strip extending in the circumferential direction) and forming longitudinal folds in the strip 210. In this manner, the strips 210 form rib-like projections that can also extend radially outward from frame 12 due to the foreshortening of the frame 12 as it expands radially.

In the illustrated embodiment, the tethers 214 are positioned radially outside of the skirt 200. In some embodiments, the tethers 214 can be positioned radially inside of the skirt 200. In other embodiments, some of the tethers 214 can be positioned outside of the skirt 200 while other tethers 214 are positioned inside of the skirt 200. When the prosthetic valve (e.g., a valve 10 with outer skirt 200) is implanted in a native annulus, the projections formed by the strips 210 can contact and form a seal against the surrounding tissue to prevent or minimize perivalvular leakage.

Figure 26:
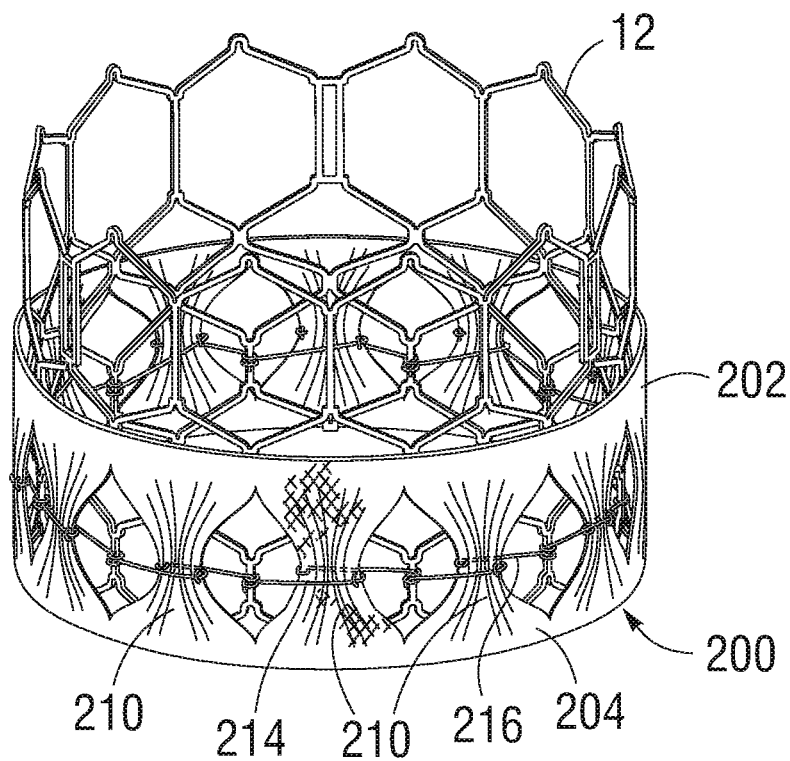
FIGS. 26-27 show another exemplary embodiment of a prosthetic heart valve frame using the outer skirt of FIGS. 22-23.
Figure 27:
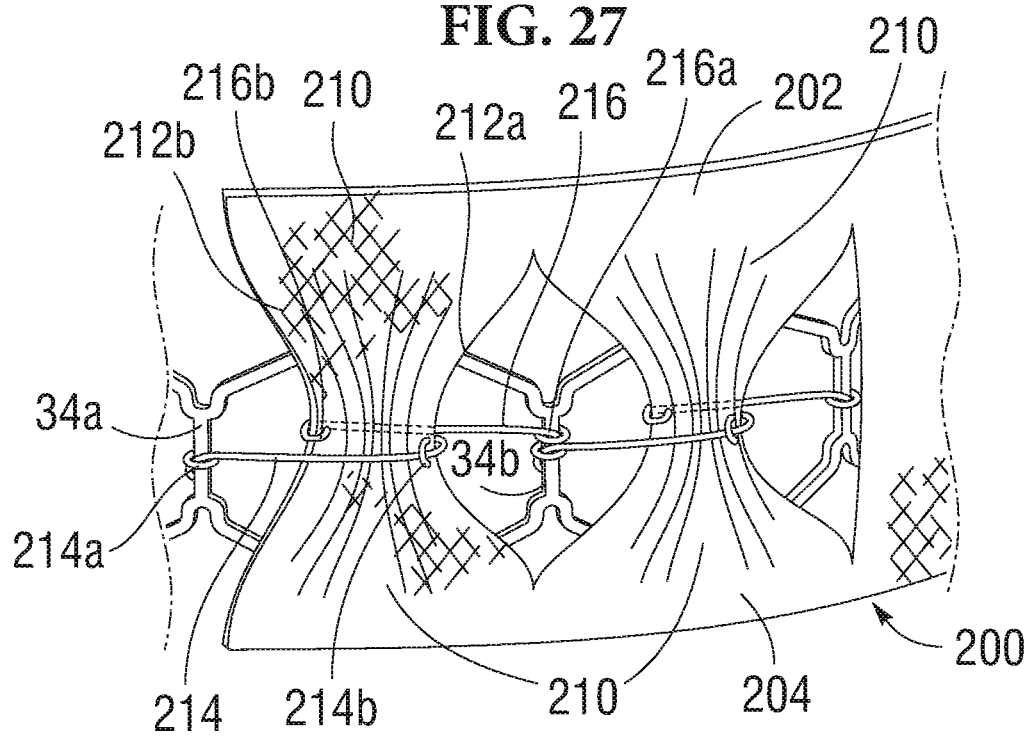

FIGS. 26-27 show another embodiment comprising a frame 12 and an outer skirt 200. The embodiment of FIGS. 26-27 is the same as the embodiment of FIGS. 24-25 except for the manner in which the skirt 200 is secured to the frame 12. As noted above with respect to the embodiment of FIGS. 24-25, the embodiment of FIGS. 26-27 can include a valvular structure, such as valvular structure 14, and an inner skirt, such as inner skirt 16, as best shown in FIGS. 1-3, to form a prosthetic heart valve. For illustrative purposes, FIGS. 26-27 only show the frame 12 and the outer skirt 200.

Referring to FIGS. 26-27, the upper and lower edge portions 202, 204 of the outer skirt 200 can be secured to the frame 12 as previously described herein. A first longitudinal edge portion 212a of each strip 210 can be secured to a strut 34a that is adjacent to a second longitudinal edge portion 212b of the same strip 210 by a first tether 214. The first tether 214 extends across the width of the strip 210 and has a first end 214a tied off or knotted around the strut 34a and a second end 214b that is secured to the edge portion 212a. The second longitudinal edge portion 212b is secured to a strut 34b that is adjacent the first edge portion 212a by a second tether 216. The second tether 216 extends across the width of the strip and has a first end 216a tied off or knotted around the strut 34b and a second end 216b secured to the second edge portion 212b.

The tethers 214, 216 desirably are on opposite sides of the skirt 200. As shown in the illustrated embodiment, the first tether 214 is positioned radially outside of the skirt 200, while the second tether 216 is positioned radially inside of the skirt 200. As such, when the frame 12 expands to a radially expanded configuration (causing struts 34a, 34b to move away from each other), the first edge portion 212a is pulled toward the second edge portion 212b by the first tether 214 and the second edge portion 212b is pulled toward the first edge portion 212a. The pulling of the tethers 214, 216 causes the width of the strip 210 to decrease and form longitudinal folds, and also causes the strip 210 to become slightly twisted or rotated by virtue of the tethers 214, 216 being on opposite sides of the outer skirt 200. As previously described, the strips 210 can also project radially away from the frame 12 due to frame foreshortening, forming rib-like projections that can help seal the prosthetic valve against the native annulus. In alternative embodiments, the tethers 214, 216 can be on the same side of the skirt 200 (i.e., both tethers 214, 216 can be positioned radially outside the skirt 200 or radially inside the skirt 200), in which case the strip 210 assumes a similar shape upon expansion of the frame but without twisting of the opposing edge portions 212a, 212b.

Figure 28:
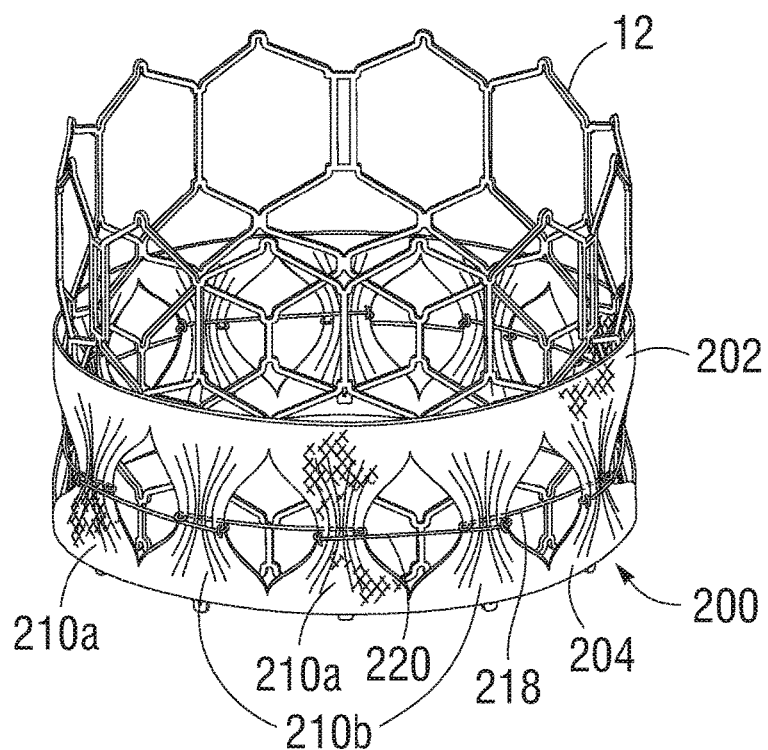
FIGS. 28-29 show another exemplary embodiment of a prosthetic heart valve frame using the outer skirt of FIGS. 22-23.
Figure 29:
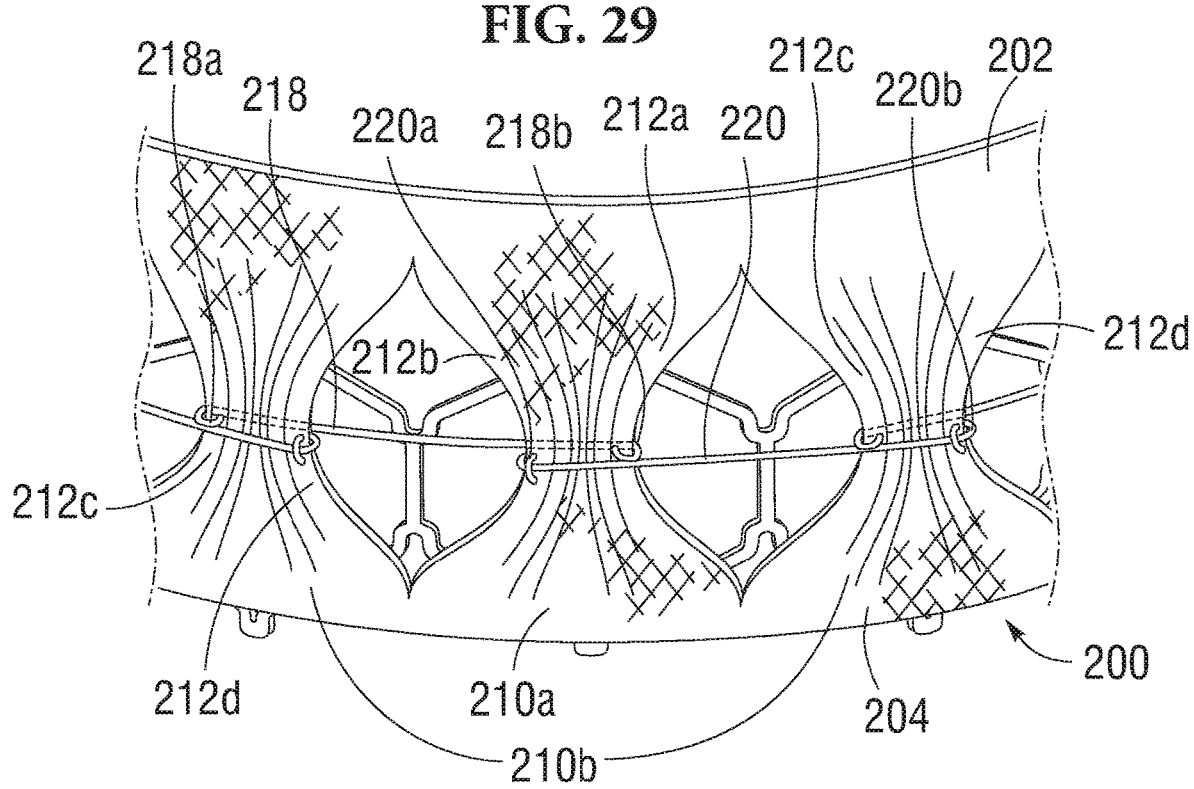

FIGS. 28-29 show another embodiment comprising a frame 12 and an outer skirt 200. The embodiment of FIGS. 28-29 is the same as the embodiment of FIGS. 24-25 except for the manner in which the skirt 200 is secured to the frame 12. As noted above with respect to the embodiment of FIGS. 24-25, the embodiment of FIGS. 28-29 can include a valvular structure, such as valvular structure 14, and an inner skirt, such as inner skirt 16, as best shown in FIGS. 1-3, to form a prosthetic heart valve. For illustrative purposes, FIGS. 28-29 only show the frame 12 and the outer skirt 200. In this embodiment, the skirt segments are coupled to each other with tethers (rather than to struts of the frame) to produce movement of the skirt segments upon radial expansion of the frame.

Referring to FIGS. 28-29, the upper and lower edge portions 202, 204 of the outer skirt 200 can be secured to the frame 12 as previously described herein. The outer skirt 200 comprises a plurality of strips 210a and 210b alternately positioned around an outer surface of the frame 12, which are similar to the strips 210 of FIGS. 24-25 except for how they are secured to the frame 12. A first longitudinal edge portion 212a of each strip 210a can be secured to a longitudinal edge portion 212c of an adjacent strip 210b by a first tether 218. The first tether 218 can extend across the width of strips 210a and 210b and can have a first end 218a secured to the edge portion 212c and a second end 218b secured to the edge portion 212a. A second longitudinal edge portion 212b of each strip 210a can be secured to a longitudinal edge portion 212d of an adjacent strip 210b on the other side of the strip 210a by a second tether 220. The second tether 220 can extend across the width of strips 210a and 210b and can have a first end 220a secured to the edge portion 212b and a second end 220b secured to the edge portion 212d. In this manner, each strip 210a is coupled to two strips 210b on opposite sides of the strip 210a by tethers 218, 220. Each strip 210b can be coupled to two strips 210a in the same manner.

The tethers 218, 220 desirably are on opposite sides of the skirt 200. As shown in the illustrated embodiment, the first tether 218 is positioned radially inside of the skirt 200, while the second tether 220 is positioned radially outside of the skirt 200. As such, when the frame 12 expands to a radially expanded configuration, the edge portions 212a, 212c of strips 210a, 210b, respectively, are pulled inwardly towards each other and the edge portions 212b, 212d of strips 210a, 210b, respectively, are pulled outwardly towards each other. The pulling of strips 210a, 210b causes the width of the strips 210a, 210b to decrease and form longitudinal folds, and also causes the strips 210a, 210b to become slightly twisted or rotated by virtue of the tethers 218, 220 being on opposite sides of the outer skirt 200. As previously described, the strips 210a, 210b can also project radially away from the frame 12 due to frame foreshortening, forming rib-like projections that can help seal the prosthetic valve against the native annulus. In alternative embodiments, the tethers 218, 220 can be on the same side of the skirt 200 (i.e., both tethers 2184, 220 can be positioned radially outside the skirt 200 or radially inside the skirt 200), in which case the strips 210a, 210b assume a similar shape upon expansion of the frame but without twisting of the opposing edge portions 212a, 212b, 212c, 212d.

In the embodiment of FIGS. 28-29, each edge portion of a strip is coupled to the farthest edge portion of an adjacent strip. In alternative embodiments, each edge portion of a strip can be coupled to the closer edge portion of an adjacent strip. For example, edge portion 212a of a strip 210a can be coupled to edge portion 212d of one strip 210b by tether 218, while edge portion 212b can be coupled to edge portion 212c by tether 220 of another strip 210b. In still other embodiments, the different techniques for coupling the skirt strips to the frame struts and to each other described above can be combined in a single prosthetic valve. For example, a skirt 200 can have some strips coupled to frame struts in the manner shown in FIGS. 24-25, some strips coupled to frame struts in the manner shown in FIGS. 26-27, and some strips coupled to each other in the manner shown in FIGS. 28-29 and/or described above.

In alternative embodiments, instead of having a single skirt mounted on the outside of the frame, the outer sealing member can comprise a plurality of discrete sealing segments positioned side-by-side around the circumference of the frame. For example, instead of cutting slits 208 in the skirt 200, the skirt 200 can be cut along cut lines extending from the lower edge to the upper edge at the locations of slits 208 in FIG. 22 to form a plurality of rectangular sealing segments. Each discrete sealing segment can be secured to the frame at its upper and lower edge portions. Each discrete sealing segment can be coupled to the frame and/or to one or more other sealing segments by one or more tethers using any of the configurations described above.

The prosthetic valve 10 can be configured for and mounted on a suitable delivery apparatus for implantation in a patient. Several catheter-based delivery apparatuses can be used; a non-limiting example of a suitable catheter-based delivery apparatus includes that disclosed in U.S. Patent Application Publication No. 2013/0030519, which is incorporated by reference herein in its entirety, and U.S. Patent Application Publication No. 2012/0123529.

In one example, to implant a plastically-expandable prosthetic valve 10 within a patient, the prosthetic valve 10, including the frame 12 and the outer skirt 200 can be crimped on an elongated shaft 180 of a delivery apparatus, as best shown in FIG. 13. The prosthetic valve, together with the delivery apparatus, can form a delivery assembly for implanting the prosthetic valve 10 in a patient's body. The shaft 180 comprises an inflatable balloon 182 for expanding the prosthetic valve within the body. With the balloon 182 deflated, the prosthetic valve 10 can then be percutaneously delivered to a desired implantation location (e.g., a native aortic valve region). Once the prosthetic valve 10 is delivered to the implantation site (e.g., the native aortic valve) inside the body, the prosthetic valve 10 can be radially expanded to its functional state by inflating the balloon 182.

Alternatively, a self-expanding prosthetic valve 10 can be crimped to a radially collapsed configuration and restrained in the collapsed configuration by inserting the prosthetic valve 10, including the frame 12 and the outer skirt 200 into a sheath or equivalent mechanism of a delivery catheter. The prosthetic valve 10 can then be percutaneously delivered to a desired implantation location. Once inside the body, the prosthetic valve 10 can be advanced from the delivery sheath, which allows the prosthetic valve 10 to expand to its functional state.

Figure 30:
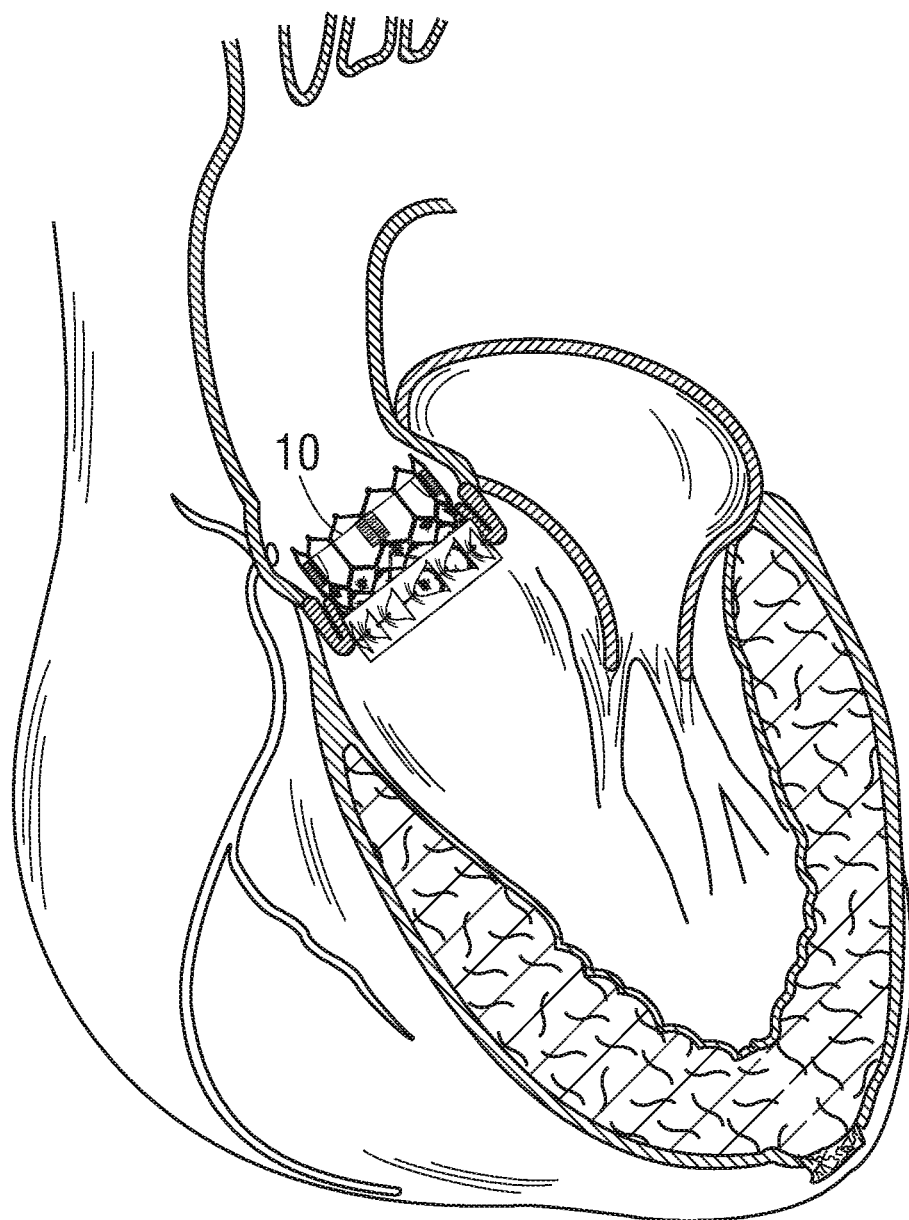
FIG. 30 shows an exemplary prosthetic heart valve implanted in the native aortic valve of a patient.

FIGS. 30-32 and 35 show various implantation positions for a prosthetic heart valve 10 having outer skirt 200 in place of outer skirt 18 as discussed above in connection with FIGS. 24-29, including implantation within a dock or anchor placed inside the patient's body prior to valve implantation. In the illustrated embodiments of FIGS. 30-31, the outer skirt 200 is configured in a manner described in connection with FIGS. 24-25. In other embodiments, the outer skirt 200 of FIGS. 30-31 can be configured in a manner described in connection with FIGS. 26-27 or in a manner described in connection with FIGS. 28-29. FIG. 30 shows the prosthetic heart valve 10 implanted in the native aortic valve of a patient.

Figure 31:
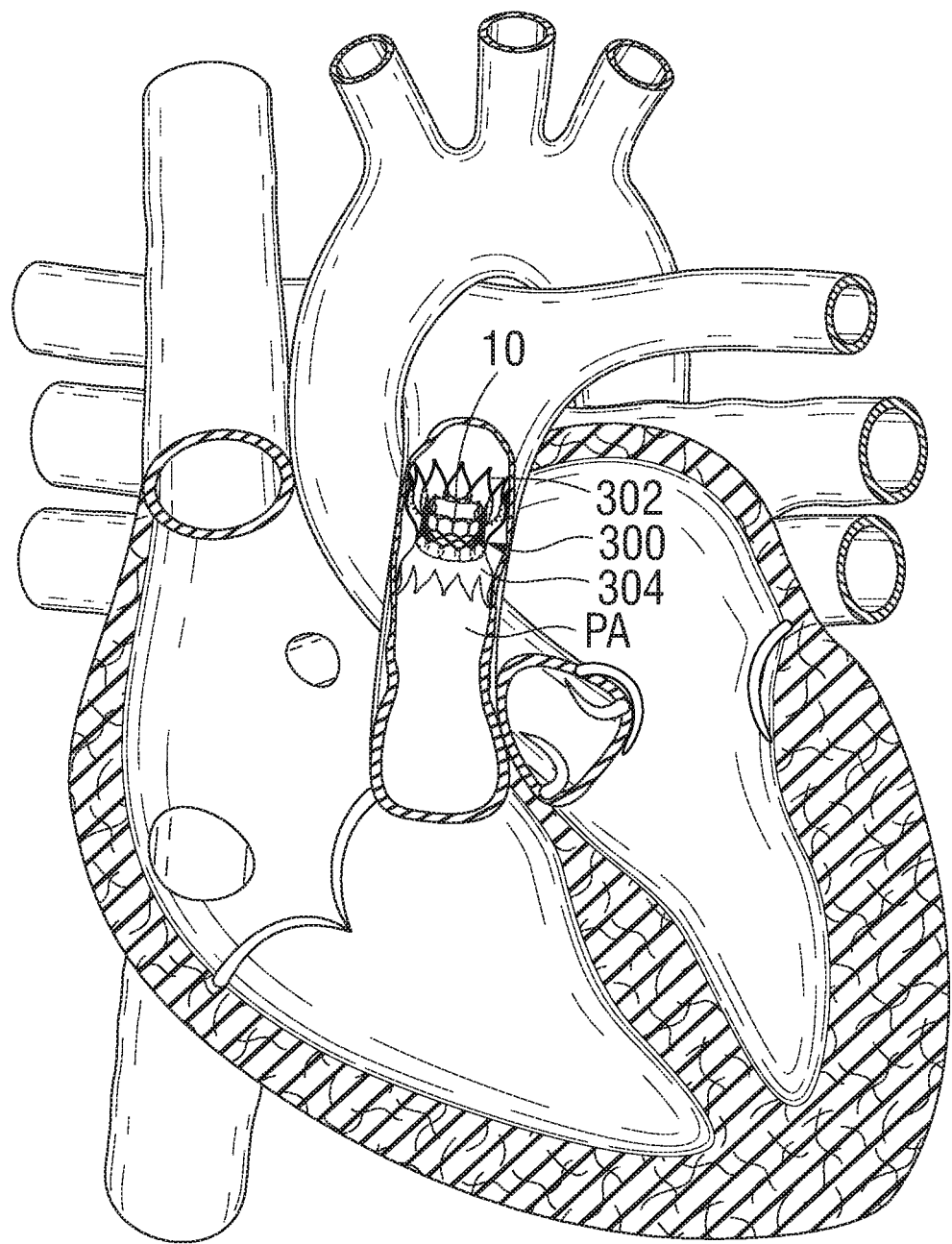
FIG. 31 shows an exemplary prosthetic heart valve and docking device implanted in the pulmonary artery of a patient.

FIG. 31 shows the prosthetic heart valve 10 implanted in the pulmonary artery of a patient for replacing or enhancing the function of a diseased pulmonary valve. Due to the variations in the size and shape of the native pulmonary valve and the pulmonary artery, the prosthetic valve 10 can be implanted within a radially expandable outer docking device 300. The docking device 300 can comprise a radially expandable and compressible annular stent 302 and a sealing member 304 that covers all or a portion of the stent and can extend across the inner surface and/or outer surface of the stent. The docking device 300 is configured to engage the inner wall of the pulmonary artery and can accommodate variations in patient anatomy. The docking device 300 also can compensate for the expanded prosthetic heart valve 310 being much smaller than vessel in which it is placed. The docking device 300 also can be used to support a prosthetic valve in other areas of the patient's anatomy, such as, the inferior vena cava, superior vena cava, or the aorta. Further details of the docking device 300 and methods for implanting the docking device and a prosthetic valve are disclosed, for example, in co-pending U.S. application Ser. No. 15/422, 354, filed Feb. 1, 2017, which is incorporated herein by reference in its entirety.

Figure 32:
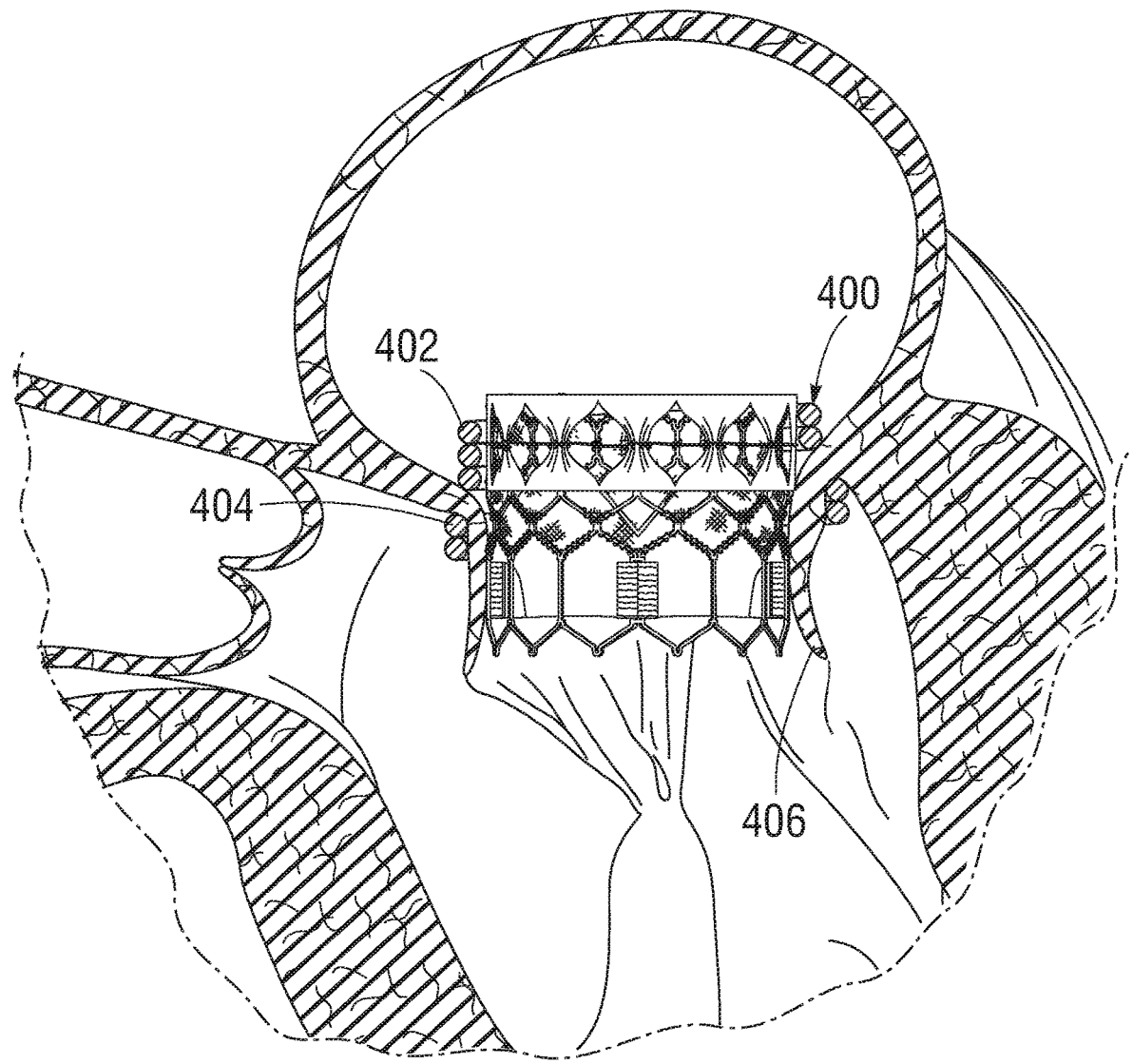
FIG. 32 shows an exemplary prosthetic heart valve and docking device implanted in the native mitral valve of a patient.

FIG. 32 shows the prosthetic heart valve 10 implanted in the native mitral valve of a patient using a docking device in the form of a helical anchor 400. The helical anchor 400 can include one or more coils 402 deployed in left atrium and one or more coils 404 deployed in the left ventricle and radially outside of the native mitral valve leaflets 406. When the prosthetic valve 10 is deployed within the native valve, the native leaflets are compressed or pinched between the prosthetic valve 410 and the anchor 400 to retain the prosthetic valve in place. Further details of the helical anchor 400 and methods for implanting the anchor and a prosthetic valve are disclosed, for example, in U.S. Application No. 62/395,940, filed Sep. 16, 2016, which is incorporated herein by reference in its entirety.

FIGS. 33 and 34 show a docking device 500 for a prosthetic heart valve, according to another embodiment. The docking device 500 can include a radially expandable and compressible frame 502 having an outer portion 504, an inner portion 506 disposed coaxially within one end portion of the outer portion 504, and a curved transition portion 508 extending between and connecting the inner portion 506 and the outer portion 504. The docking device 500 can further include a sealing member 510 extending over the inner surface of the inner portion 506, a portion of the outer surface of the outer portion 504 adjacent the inner portion 506, and the transition portion 508.

Figure 35:
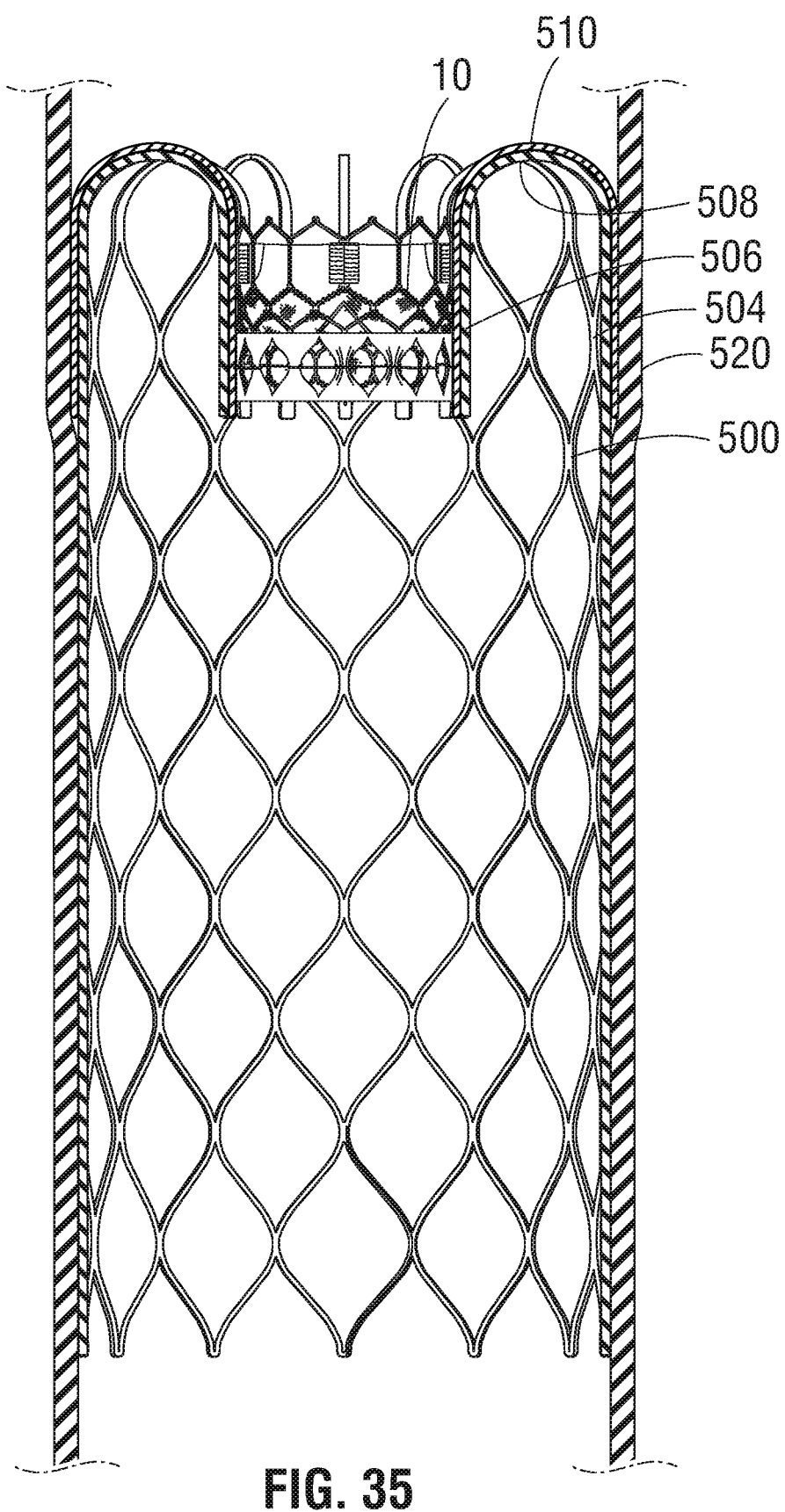
FIG. 35 shows an exemplary prosthetic heart valve and the docking device of FIGS. 33-34.

FIG. 35 shows the docking device 500 implanted in a vessel 520, which can be, for example, the inferior vena cava, superior vena cava, or the ascending aorta. As shown, a prosthetic valve 10 can be deployed within the inner portion 506 of the docking device 500. Similar to the docking device 300, the docking device 500 can compensate for the expanded prosthetic heart valve 10 being much smaller than vessel in which it is placed. The docking device 500 is particularly suited for implanting a prosthetic valve in the inferior vena cava for replacing or enhancing the function of the native tricuspid valve. Further details of the docking device 500 and methods for implanting the docking device and a prosthetic valve are disclosed, for example, in co-pending U.S. application Ser. No. 16/034,794, filed Jul. 13, 2018, which is incorporated herein by reference.

General Considerations

It should be understood that the disclosed valves can be implanted in any of the native annuluses of the heart (e.g., the pulmonary, mitral, and tricuspid annuluses), and can be used with any of various approaches (e.g., retrograde, antegrade, transseptal, transventricular, transatrial, etc.). The disclosed prostheses can also be implanted in other lumens of the body.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

As used in this application and in the claims, the singular forms "a," "an," and "the" include the plural forms unless the context clearly dictates otherwise. Additionally, the term "includes" means "comprises."

As used herein, the term "and/or" used between the last two of a list of elements means any one or more of the listed elements. For example, the phrase "A, B, and/or C" means "A", "B", "C", "A and B", "A and C", "B and C", or "A, B, and C".

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "coupled" and "associated" generally mean physically coupled or linked and does not exclude the presence of intermediate elements between the coupled or associated items absent specific contrary language.

As used herein, operations that occur "simultaneously" or "concurrently" occur generally at the same time as one another, although delays in the occurrence of one operation relative to the other due to, for example, spacing, play or backlash between components in a mechanical linkage such as threads, gears, etc., are expressly within the scope of the above terms, absent specific contrary language.

In view of the many possible embodiments to which the principles disclosed herein may be applied, it should be recognized that the illustrated embodiments are only preferred examples and should not be taken as limiting the scope of the disclosure. Rather, the scope of the disclosure is at least as broad as the following claims.

I claim:

1. An implantable prosthetic valve comprising:
   an annular frame comprising an inflow end and an outflow end and being radially collapsible and expandable between a radially collapsed configuration and a radially expanded configuration, the frame defining an axial direction extending from the inflow end to the outflow end;
   a leaflet structure positioned within the frame and secured thereto; and
   an outer sealing member positioned around an outer surface of the frame, wherein the outer sealing member comprises a plurality of sealing segments;
   wherein each sealing segment is coupled to the frame and/or another sealing segment by a tether that pulls a portion of the sealing segment in a circumferential direction when the frame is radially expanded to the expanded configuration.

2. The prosthetic valve of claim 1, wherein each sealing segment has upper and lower portions connected to the frame at axially spaced apart locations on the frame that move toward each other upon radial expansion of the frame and cause a portion of the sealing segment to move radially outwardly away from the frame.

3. The prosthetic valve of claim 1, wherein the plurality of sealing segments are formed by a plurality of circumferentially spaced apart slits in the outer sealing member and wherein the plurality of sealing segments are connected to each other at upper and lower ends by an upper edge portion and a lower edge portion of the outer sealing member.

4. The prosthetic valve of claim 1, wherein the plurality of sealing segments are discrete sealing segments that are positioned side-by-side around a circumference of the frame.

5. The prosthetic valve of claim 1, wherein a width of each sealing segment in the circumferential direction is reduced by a pulling force of the tether connected to the sealing segment upon radial expansion of the frame.

6. The prosthetic valve of claim 1, wherein each sealing segment becomes at least partially twisted by a pulling force of the tether connected to the sealing segment upon radial expansion of the frame.

7. The prosthetic valve of claim 1, wherein the tether has a first end secured to the sealing segment and a second end secured to the frame or another sealing segment of the plurality of sealing segments.

8. The prosthetic valve of claim 7, wherein the first end of the tether is secured to a first longitudinal edge portion of the sealing segment and the second end of the tether is secured to a strut of the frame that is arranged closest to an opposing, second longitudinal edge portion of the sealing segment.

9. The prosthetic valve of claim 1, wherein the tether is a first tether and wherein each sealing segment is further coupled to the frame and/or another sealing segment by a second tether.

10. The prosthetic valve of claim 9, wherein a first end of the first tether is secured to a first longitudinal edge portion of the sealing segment and a second end of the first tether is secured to a first strut of the frame that is arranged adjacent to an opposing, second longitudinal edge portion of the sealing segment, wherein a first end of the second tether is secured to the second longitudinal edge portion of the sealing segment and a second end of the second tether is secured to a second strut of the frame that is arranged adjacent to the first longitudinal edge portion of the sealing segment, and wherein the first strut and the second strut are axially extending struts of the frame and form a portion of a same cell of the frame.

11. The prosthetic valve of claim 9, wherein each sealing segment is arranged adjacent to and between, in the circumferential direction, a first adjacent sealing segment and a second adjacent sealing segment of the plurality of sealing segments and wherein the sealing segment is coupled to the first adjacent sealing segment by the first tether and coupled to the second adjacent sealing segment by the second tether, wherein each of the first tether and the second tether extends across a width of the sealing segment, the width arranged in the circumferential direction.

12. The prosthetic valve of claim 11, wherein a first end of the first tether is secured to a first longitudinal edge portion of the sealing segment and a second end of the first tether is secured to a second longitudinal edge portion of the first adjacent sealing segment and wherein a first end of the second tether is secured to a second longitudinal edge portion of the sealing segment and a second end of the second tether is secured to a first longitudinal edge portion of the second adjacent sealing segment.

13. An implantable prosthetic valve comprising:
an annular frame comprising an inflow end and an outflow end and being radially collapsible and expandable between a radially collapsed configuration and a radially expanded configuration, the frame defining an axial direction extending from the inflow end to the outflow end;
a leaflet structure positioned within the frame and secured thereto; and
an outer sealing member positioned around an outer surface of the frame, wherein the outer sealing member comprises a plurality of sealing segments;
wherein each sealing segment is coupled to the frame and/or another sealing segment by a first tether that pulls a first longitudinal edge portion of the sealing segment in a first circumferential direction and a second tether that pulls a second longitudinal edge portion of the sealing segment in a second circumferential direction, when the frame is radially expanded to the expanded configuration.

14. The implantable prosthetic valve of claim 13, wherein, for each sealing segment, the first tether is secured to the first longitudinal edge portion of the sealing segment and a first strut of the frame that is arranged adjacent to the second longitudinal edge portion of the sealing segment and the second tether is secured to the second longitudinal edge portion and a second strut that is arranged adjacent to the first longitudinal edge portion.

15. The implantable prosthetic valve of claim 13, wherein, for each sealing segment, the first tether is secured to the first longitudinal edge portion of the sealing segment and a second longitudinal edge portion of a first adjacent sealing segment of the plurality of sealing segments and the second tether is secured to the second longitudinal edge portion of the sealing segment and a first longitudinal edge portion of a second adjacent sealing segment, wherein each of the first tether and the second tether extend across a width of the sealing segment, the width arranged in the first and second circumferential directions.

16. The implantable prosthetic valve of claim 13, wherein, for each sealing segment, the first tether and the second tether are configured to reduce a width of a portion of the sealing segment arranged between an upper edge portion and a lower edge portion of the outer sealing member and create longitudinal folds in the sealing segment.

17. The implantable prosthetic valve of claim 13, wherein the first tether is positioned radially inside of the outer sealing member and the second tether is positioned radially outside of the outer sealing member, relative to a radial direction that is arranged perpendicular to the axial direction.

18. An implantable prosthetic valve comprising:
an annular frame comprising an inflow end and an outflow end and being radially collapsible and expandable between a radially collapsed configuration and a radially expanded configuration, the frame defining an axial direction extending from the inflow end to the outflow end;
a leaflet structure positioned within the frame and secured thereto; and
an outer sealing member positioned around an outer surface of the frame, wherein the outer sealing member comprises a plurality of sealing segments, wherein each sealing segment extends longitudinally, in the axial direction, between an upper edge portion and a lower edge portion of the outer sealing member and has a width defined between a first longitudinal edge portion and a second longitudinal edge of the sealing segment; and
wherein each sealing segment is coupled to the frame and/or another sealing segment by at least a first tether that pulls a portion of the sealing segment in a circumferential direction such that the width of the sealing segment between its upper and lower ends decreases and forms longitudinal folds in the sealing segment when the frame is radially expanded to the expanded configuration, wherein the portion of the sealing segment is one of the first longitudinal edge portion and the second longitudinal edge portion of the sealing segment.

19. The implantable prosthetic valve of claim 18, wherein the first tether is coupled to the first longitudinal edge portion of the sealing segment and wherein each sealing segment is coupled to the frame and/or another sealing segment by a second tether that pulls the second longitudinal edge portion of the sealing segment in the circumferential direction when the frame is radially expanded to the expanded configuration.

20. The implantable prosthetic valve of claim 19, wherein the first tether and the second tether are arranged on opposite sides of the outer sealing member, relative to a radial direction that is arranged perpendicular to the axial direction and the width.

* * * * *